(12) United States Patent
Fruerlund et al.

(10) Patent No.: US 11,684,767 B2
(45) Date of Patent: *Jun. 27, 2023

(54) INFUSION TUBE SYSTEM AND METHOD FOR MANUFACTURE

(71) Applicant: UnoMedical A/S, Lejre (DK)

(72) Inventors: Peter Fruerlund, Solrød (DK); Jacob Andersen, Næstved (DK)

(73) Assignee: UNOMEDICAL A/S, Lejre (DK)

( * ) Notice: Subject to any disclaimer, the term of this patent is extended or adjusted under 35 U.S.C. 154(b) by 71 days.

This patent is subject to a terminal disclaimer.

(21) Appl. No.: 17/398,535

(22) Filed: Aug. 10, 2021

(65) Prior Publication Data

US 2021/0370039 A1    Dec. 2, 2021

Related U.S. Application Data

(63) Continuation of application No. 15/282,825, filed on Sep. 30, 2016, now Pat. No. 11,110,261, which is a
(Continued)

(30) Foreign Application Priority Data

Oct. 19, 2011 (EP) ........................................ 1185747

(51) Int. Cl.
*A61M 39/10* (2006.01)
*A61M 39/20* (2006.01)
*A61M 5/38* (2006.01)

(52) U.S. Cl.
CPC ............. *A61M 39/10* (2013.01); *A61M 5/385* (2013.01); *A61M 2039/205* (2013.01); *A61M 2207/00* (2013.01); *Y10T 156/10* (2015.01)

(58) Field of Classification Search
CPC ...... A61M 39/10; A61M 39/12; A61M 39/20; A61M 2039/205; A61J 1/20; A61J 1/2003;
(Continued)

(56) References Cited

U.S. PATENT DOCUMENTS 1,592,462 A    7/1926  Maccregor
2,047,010 A    7/1936  Dickinson
(Continued)

FOREIGN PATENT DOCUMENTS

DE    1011728 B    7/1957
DE    4342329 A1   6/1994
(Continued)

OTHER PUBLICATIONS

PCT/EP2012/070462 International Preliminary Report on Patentability dated Apr. 22, 2014.
(Continued)

*Primary Examiner* — Amber R Stiles
*Assistant Examiner* — Leah J Swanson
(74) *Attorney, Agent, or Firm* — Taft Stettinius & Hollister LLP; Derek B. Lavender; Ryan O. White (57) ABSTRACT

An infusion tube system and a method for manufacture are provided. An infusion tube system including an infusion tube and a connector attached to the infusion tube at an end of the infusion tube is disclosed. The connector has a proximal end and includes a connector body extending from a distal end to a proximal end along a center axis and defining a cavity. The connector body includes an end wall with an inner surface, and at least one vent opening, and a sidewall extending from the end wall along the center axis with an inner and outer surface. The connector includes a membrane covering the at least one vent opening, the membrane being welded to the inner surface of the end wall along at least one welding seam including a first welding seam such that the membrane covers and seals the at least one vent opening.

10 Claims, 7 Drawing Sheets

Related U.S. Application Data continuation of application No. 13/652,722, filed on Oct. 16, 2012, now abandoned.

(60) Provisional application No. 61/548,871, filed on Oct. 19, 2011.

(58) Field of Classification Search
CPC ........ A61J 1/2006; A61J 1/201; A61J 1/2048;
A61J 1/2089; A61J 1/2096; A61J 1/2068;
A61J 1/2072; A61J 1/2075; A61J 1/2079;
A61J 1/2082; A61J 1/2086
See application file for complete search history.

(56) References Cited

U.S. PATENT DOCUMENTS

| | | |
|---|---|---|
| 2,295,849 A | 9/1942 | Kayden |
| 2,690,529 A | 9/1954 | Lindblad |
| 2,972,779 A | 2/1961 | Cowley |
| 3,059,802 A | 10/1962 | Mitchell |
| 3,074,541 A | 1/1963 | Roehr |
| 3,149,186 A | 9/1964 | Coanda |
| 3,221,739 A | 12/1965 | Rosenthal |
| 3,221,740 A | 12/1965 | Rosenthal |
| 3,306,291 A | 2/1967 | Burke |
| 3,485,352 A | 12/1969 | Nicholas |
| 3,509,879 A | 5/1970 | Louis et al. |
| 3,519,158 A | 7/1970 | Douglas |
| 3,547,119 A | 12/1970 | John et al. |
| 3,575,337 A | 4/1971 | Daniel |
| 3,610,240 A | 10/1971 | Andrew |
| 3,615,039 A | 10/1971 | Frank |
| 3,670,727 A | 6/1972 | Donald |
| 3,783,895 A | 1/1974 | Weichselbaum |
| 3,788,374 A | 1/1974 | Saijo |
| 3,810,469 A | 5/1974 | Hurschman |
| 3,835,862 A | 9/1974 | Villari |
| 3,840,011 A | 10/1974 | Wright |
| 3,893,448 A | 7/1975 | Brantigan |
| 3,937,219 A | 2/1976 | Karakashian |
| 3,986,507 A | 10/1976 | Watt |
| 3,986,508 A | 10/1976 | Barrington |
| 3,995,518 A | 12/1976 | Spiroff |
| 4,022,205 A | 5/1977 | Tenczar |
| 4,188,950 A | 2/1980 | Wardlaw |
| 4,201,406 A | 5/1980 | Dennehey et al. |
| 4,227,528 A | 10/1980 | Wardlaw |
| 4,259,276 A | 3/1981 | Rawlings |
| 4,267,836 A | 5/1981 | Whiteny et al. |
| 4,296,786 A | 10/1981 | Brignola |
| 4,315,505 A | 2/1982 | Crandall et al. |
| 4,333,455 A | 6/1982 | Bodicky |
| 4,334,551 A | 6/1982 | Pfister |
| D267,199 S | 12/1982 | Koenig |
| 4,378,015 A | 3/1983 | Wardlaw |
| 4,402,407 A | 9/1983 | Maly |
| 4,415,393 A | 11/1983 | Grimes |
| 4,417,886 A | 11/1983 | Frankhouser et al. |
| 4,464,178 A | 8/1984 | Dalton |
| 4,473,369 A | 9/1984 | Lueders et al. |
| 4,484,910 A | 11/1984 | Sarnoff et al. |
| 4,500,312 A | 2/1985 | McFarlane |
| 4,508,367 A | 4/1985 | Oreopoulos et al. |
| 4,525,157 A | 6/1985 | Vaillancourt |
| 4,530,695 A | 7/1985 | Phillips et al. |
| 4,531,937 A | 7/1985 | Yates |
| 4,543,088 A | 9/1985 | Bootman et al. |
| 4,563,177 A | 1/1986 | Kamen |
| 4,610,469 A | 9/1986 | Wolff-Mooij |
| 4,617,019 A | 10/1986 | Fecht et al. |
| 4,713,059 A | 12/1987 | Bickelhaupt et al. |
| 4,734,092 A | 3/1988 | Millerd |
| 4,755,173 A | 7/1988 | Konopka et al. |
| 4,817,603 A | 4/1989 | Turner et al. |
| RE32,922 E | 5/1989 | Levin et al. |
| 4,838,871 A | 6/1989 | Luther |
| 4,840,613 A | 6/1989 | Balbierz |
| 4,850,974 A | 7/1989 | Bickelhaupt et al. |
| 4,850,996 A | 7/1989 | Cree |
| 4,863,016 A | 9/1989 | Fong et al. |
| 4,878,897 A | 11/1989 | Katzin |
| 4,890,608 A | 1/1990 | Steer |
| 4,894,054 A | 1/1990 | Miskinyar |
| 4,895,570 A | 1/1990 | Larkin |
| 4,917,669 A | 4/1990 | Bonaldo |
| 4,935,010 A | 6/1990 | Cox et al. |
| 4,950,163 A | 8/1990 | Zimble |
| 4,950,252 A | 8/1990 | Luther et al. |
| 4,956,989 A | 9/1990 | Nakajima |
| 4,970,954 A | 11/1990 | Weir et al. |
| 4,978,338 A | 12/1990 | Melsky et al. |
| 4,982,842 A | 1/1991 | Hollister |
| 4,986,817 A | 1/1991 | Code |
| 4,994,042 A | 2/1991 | Vadher |
| 4,994,045 A | 2/1991 | Ranford |
| 5,011,475 A | 4/1991 | Olson |
| 5,011,555 A | 4/1991 | Sager et al. |
| 5,020,665 A | 6/1991 | Bruno |
| 5,024,662 A | 6/1991 | Menes et al. |
| 5,067,496 A | 11/1991 | Eisele |
| 5,092,853 A | 3/1992 | Couvertier, II |
| 5,098,389 A | 3/1992 | Cappucci |
| 5,112,313 A | 5/1992 | Sallee |
| 5,116,319 A | 5/1992 | van den Haak |
| 5,116,325 A | 5/1992 | Paterson |
| 5,121,751 A | 6/1992 | Panalletta |
| 5,129,884 A | 7/1992 | Dysarz |
| 5,135,502 A | 8/1992 | Koenig, Jr. et al. |
| 5,137,516 A | 8/1992 | Rand et al. |
| 5,137,524 A | 8/1992 | Lynn et al. |
| 5,141,496 A | 8/1992 | Dalto et al. |
| 5,147,375 A | 9/1992 | Sullivan et al. |
| 5,163,915 A | 11/1992 | Holleron |
| 5,172,808 A | 12/1992 | Bruno |
| 5,176,643 A | 1/1993 | Kramer et al. |
| 5,176,650 A | 1/1993 | Haining |
| 5,176,662 A | 1/1993 | Bartholomew et al. |
| 5,186,712 A | 2/1993 | Kelso et al. |
| 5,188,611 A | 2/1993 | Orgain |
| RE34,223 E | 4/1993 | Bonaldo |
| 5,205,820 A | 4/1993 | Kriesel |
| 5,215,529 A | 6/1993 | Fields et al. |
| 5,222,947 A | 6/1993 | D'Amico |
| 5,232,454 A | 8/1993 | Hollister |
| 5,248,301 A | 9/1993 | Koenig, Jr. et al. |
| 5,256,149 A | 10/1993 | Banik et al. |
| 5,256,152 A | 10/1993 | Marks |
| 5,257,980 A | 11/1993 | Van et al. |
| 5,267,963 A | 12/1993 | Bachynsky |
| 5,269,799 A | 12/1993 | Daniel |
| 5,271,744 A | 12/1993 | Kramer et al. |
| 5,279,579 A | 1/1994 | D'Amico |
| 5,279,591 A | 1/1994 | Simon |
| 5,282,793 A | 2/1994 | Larson |
| 5,300,030 A | 4/1994 | Crossman et al. |
| 5,312,359 A | 5/1994 | Wallace |
| 5,312,369 A | 5/1994 | Arcusin et al. |
| 5,316,246 A | 5/1994 | Scott et al. |
| 5,324,302 A | 6/1994 | Crouse |
| 5,342,319 A | 8/1994 | Watson et al. |
| 5,342,324 A | 8/1994 | Tucker |
| 5,344,007 A | 9/1994 | Nakamura et al. |
| 5,350,392 A | 9/1994 | Purcell et al. |
| 5,354,280 A | 10/1994 | Haber et al. |
| 5,354,337 A | 10/1994 | Hoy |
| 5,366,469 A | 11/1994 | Steg et al. |
| 5,372,592 A | 12/1994 | Gambale |
| 5,372,787 A | 12/1994 | Ritter |
| 5,376,082 A | 12/1994 | Phelps |
| 5,379,895 A | 1/1995 | Foslien |
| 5,384,174 A | 1/1995 | Ward et al. |
| 5,387,197 A | 2/1995 | Smith et al. |
| 5,390,669 A | 2/1995 | Stuart et al. |
| 5,391,151 A | 2/1995 | Wilmot |

(56) References Cited

U.S. PATENT DOCUMENTS

| | | |
|---|---|---|
| 5,403,288 A | 4/1995 | Stanners |
| 5,405,332 A | 4/1995 | Opalek |
| 5,425,715 A | 6/1995 | Dalling et al. |
| 5,429,607 A | 7/1995 | McPhee |
| 5,429,613 A | 7/1995 | D'Amico |
| 5,439,473 A | 8/1995 | Jorgensen |
| D362,718 S | 9/1995 | Deily et al. |
| 5,449,349 A | 9/1995 | Sallee et al. |
| 5,451,210 A | 9/1995 | Kramer et al. |
| 5,478,316 A | 12/1995 | Bitdinger et al. |
| 5,490,841 A | 2/1996 | Landis |
| 5,501,675 A | 3/1996 | Erskine |
| 5,505,709 A | 4/1996 | Funderburk et al. |
| 5,507,730 A | 4/1996 | Haber et al. |
| 5,514,117 A | 5/1996 | Lynn |
| 5,520,654 A | 5/1996 | Wahlberg |
| 5,522,803 A | 6/1996 | Teissen-Simony |
| 5,527,287 A | 6/1996 | Miskinyar |
| 5,533,974 A | 7/1996 | Gaba |
| 5,540,709 A | 7/1996 | Ramel |
| 5,545,143 A | 8/1996 | Fischell |
| 5,545,152 A | 8/1996 | Funderburk et al. |
| 5,549,577 A | 8/1996 | Siegel et al. |
| 5,554,130 A | 9/1996 | McDonald et al. |
| 5,558,650 A | 9/1996 | McPhee |
| 5,562,629 A | 10/1996 | Haughton et al. |
| 5,562,636 A | 10/1996 | Utterberg |
| 5,573,510 A | 11/1996 | Isaacson |
| 5,575,777 A | 11/1996 | Cover et al. |
| 5,584,813 A | 12/1996 | Livingston et al. |
| 5,586,553 A | 12/1996 | Halili et al. |
| 5,591,188 A | 1/1997 | Waisman |
| 5,599,309 A | 2/1997 | Marshall et al. |
| 5,599,315 A | 2/1997 | McPhee |
| 5,599,318 A | 2/1997 | Sweeney et al. |
| 5,628,765 A | 5/1997 | Morita |
| 5,643,214 A | 7/1997 | Marshall et al. |
| 5,643,216 A | 7/1997 | White |
| 5,643,220 A | 7/1997 | Cosme |
| 5,658,256 A | 8/1997 | Shields |
| 5,662,617 A | 9/1997 | Odell et al. |
| 5,665,071 A | 9/1997 | Wyrick |
| 5,665,075 A | 9/1997 | Gyure et al. |
| 5,676,156 A | 10/1997 | Yoon |
| 5,681,323 A | 10/1997 | Arick |
| 5,695,476 A | 12/1997 | Harris |
| 5,697,907 A | 12/1997 | Gaba |
| 5,700,250 A | 12/1997 | Erskine |
| 5,700,695 A | 12/1997 | Yassinzadeh et al. |
| 5,702,371 A | 12/1997 | Bierman |
| 5,704,920 A | 1/1998 | Gyure |
| 5,709,662 A | 1/1998 | Olive et al. |
| 5,714,225 A | 2/1998 | Hansen et al. |
| 5,738,641 A | 4/1998 | Watson et al. |
| 5,741,288 A | 4/1998 | Rife |
| 5,752,923 A | 5/1998 | Terwilliger |
| 5,807,316 A | 9/1998 | Teeple, Jr. |
| 5,807,348 A | 9/1998 | Zinger et al. |
| 5,810,835 A | 9/1998 | Ryan et al. |
| 5,817,058 A | 10/1998 | Shaw |
| 5,820,598 A | 10/1998 | Gazza et al. |
| 5,827,236 A | 10/1998 | Takahashi |
| 5,833,666 A | 11/1998 | Davis et al. |
| 5,843,001 A | 12/1998 | Goldenberg |
| 5,848,990 A | 12/1998 | Cirelli et al. |
| 5,851,197 A | 12/1998 | Marano et al. |
| 5,858,001 A | 1/1999 | Tsals et al. |
| 5,865,806 A | 2/1999 | Howell |
| 5,899,886 A | 5/1999 | Cosme |
| 5,911,705 A | 6/1999 | Howell |
| 5,913,846 A | 6/1999 | Szabo |
| 5,916,199 A | 6/1999 | Miles |
| 5,919,167 A | 7/1999 | Mulhauser et al. |
| 5,919,170 A | 7/1999 | Woessner |
| 5,925,032 A | 7/1999 | Clements |
| 5,935,109 A | 8/1999 | Donnan |
| 5,947,931 A | 9/1999 | Bierman |
| 5,947,935 A | 9/1999 | Rhinehart et al. |
| 5,951,523 A | 9/1999 | Oesterlind et al. |
| 5,954,643 A | 9/1999 | Vanantwerp et al. |
| 5,957,892 A | 9/1999 | Thorne |
| 5,957,897 A | 9/1999 | Jeffrey |
| 5,968,011 A | 10/1999 | Larsen et al. |
| 5,971,966 A | 10/1999 | Lav |
| 5,975,120 A | 11/1999 | Novosel |
| 5,980,488 A | 11/1999 | Thorne |
| 5,980,506 A | 11/1999 | Mathiasen |
| 5,984,224 A | 11/1999 | Yang |
| 5,984,897 A | 11/1999 | Petersen et al. |
| D417,733 S | 12/1999 | Howell et al. |
| 6,017,328 A | 1/2000 | Fischell et al. |
| 6,017,598 A | 1/2000 | Kreischer et al. |
| D421,119 S | 2/2000 | Musgrave et al. |
| 6,024,727 A | 2/2000 | Thorne et al. |
| 6,039,629 A | 3/2000 | Mitchell |
| 6,042,570 A | 3/2000 | Bell et al. |
| 6,045,533 A | 4/2000 | Kriesel et al. |
| 6,045,534 A | 4/2000 | Jacobsen et al. |
| 6,050,976 A | 4/2000 | Thorne et al. |
| 6,053,893 A | 4/2000 | Bucher |
| 6,053,930 A | 4/2000 | Ruppert |
| 6,056,718 A | 5/2000 | Funderburk et al. |
| 6,056,726 A | 5/2000 | Isaacson |
| 6,074,369 A | 6/2000 | Sage et al. |
| 6,074,371 A | 6/2000 | Fischell |
| 6,077,244 A | 6/2000 | Botich et al. |
| 6,079,432 A | 6/2000 | Paradis |
| 6,086,008 A | 7/2000 | Gray et al. |
| 6,086,575 A | 7/2000 | Mejslov |
| 6,090,068 A | 7/2000 | Chanut |
| 6,093,172 A | 7/2000 | Funderburk et al. |
| 6,093,179 A | 7/2000 | O'Hara et al. |
| 6,099,503 A | 8/2000 | Stradella |
| 6,105,218 A | 8/2000 | Reekie |
| 6,120,482 A | 9/2000 | Szabo |
| 6,123,690 A | 9/2000 | Mejslov |
| 6,132,755 A | 10/2000 | Eicher et al. |
| 6,139,534 A | 10/2000 | Niedospial, Jr. et al. |
| 6,159,181 A | 12/2000 | Crossman et al. |
| 6,183,421 B1 | 2/2001 | Bobo |
| 6,183,464 B1 | 2/2001 | Sharp et al. |
| 6,191,338 B1 | 2/2001 | Haller |
| 6,193,694 B1 | 2/2001 | Bell et al. |
| 6,210,420 B1 | 4/2001 | Mauze et al. |
| 6,219,574 B1 | 4/2001 | Cormier et al. |
| 6,221,058 B1 | 4/2001 | Kao et al. |
| 6,248,093 B1 | 6/2001 | Moberg |
| 6,261,272 B1 | 7/2001 | Gross et al. |
| 6,293,925 B1 | 9/2001 | Safabash et al. |
| 6,302,866 B1 | 10/2001 | Marggi |
| 6,319,232 B1 | 11/2001 | Kashmer |
| 6,322,535 B1 | 11/2001 | Hitchins et al. |
| 6,322,808 B1 | 11/2001 | Trautman et al. |
| 6,334,856 B1 | 1/2002 | Allen et al. |
| 6,355,021 B1 | 3/2002 | Nielsen et al. |
| 6,364,113 B1 | 4/2002 | Faasse, Jr. et al. |
| 6,378,218 B2 | 4/2002 | Sigwart et al. |
| 6,379,335 B1 | 4/2002 | Rigon et al. |
| 6,387,076 B1 | 5/2002 | Landuyt |
| 6,387,078 B1 | 5/2002 | Gillespie, III |
| 6,405,876 B1 | 6/2002 | Seshimoto et al. |
| 6,440,096 B1 | 8/2002 | Lastovich et al. |
| 6,447,482 B1 | 9/2002 | Roenborg et al. |
| 6,450,992 B1 | 9/2002 | Cassidy, Jr. |
| 6,485,461 B1 | 11/2002 | Mason et al. |
| 6,488,663 B1 | 12/2002 | Steg |
| 6,503,222 B1 | 1/2003 | Lo |
| 6,517,517 B1 | 2/2003 | Farrugia et al. |
| 6,520,938 B1 | 2/2003 | Funderburk et al. |
| D472,316 S | 3/2003 | Douglas et al. |
| D472,630 S | 4/2003 | Douglas et al. |
| 6,572,586 B1 | 6/2003 | Wojcik |
| 6,579,267 B2 | 6/2003 | Lynch et al. |
| 6,582,397 B2 | 6/2003 | Alesi et al. |

(56) References Cited

U.S. PATENT DOCUMENTS

| | | |
|---|---|---|
| 6,595,962 B1 | 7/2003 | Perthu |
| 6,607,509 B2 | 8/2003 | Bobroff et al. |
| 6,607,511 B2 | 8/2003 | Halseth et al. |
| 6,613,064 B2 | 9/2003 | Rutynowski et al. |
| 6,620,133 B1 | 9/2003 | Steck |
| 6,620,136 B1 | 9/2003 | Pressly, Sr. et al. |
| 6,620,140 B1 | 9/2003 | Metzger |
| 6,629,949 B1 | 10/2003 | Douglas |
| 6,645,181 B1 | 11/2003 | Maynard |
| 6,645,182 B1 | 11/2003 | Szabo |
| 6,659,982 B2 | 12/2003 | Douglas et al. |
| 6,685,674 B2 | 2/2004 | Douglas et al. |
| 6,699,218 B2 | 3/2004 | Flaherty et al. |
| 6,702,779 B2 | 3/2004 | Connelly et al. |
| 6,726,649 B2 | 4/2004 | Swenson et al. |
| 6,736,797 B1 | 5/2004 | Larsen et al. |
| 6,743,203 B1 | 6/2004 | Pickhard |
| 6,749,587 B2 | 6/2004 | Flaherty |
| 6,749,589 B1 | 6/2004 | Douglas et al. |
| 6,755,805 B1 | 6/2004 | Reid |
| 6,776,775 B1 | 8/2004 | Mohammad |
| 6,790,199 B1 | 9/2004 | Gianakos |
| 6,805,686 B1 | 10/2004 | Fathallah et al. |
| 6,808,506 B2 | 10/2004 | Lastovich et al. |
| 6,811,545 B2 | 11/2004 | Vaillancourt |
| 6,814,720 B2 | 11/2004 | Olsen et al. |
| 6,824,530 B2 | 11/2004 | Wagner et al. |
| 6,824,531 B1 | 11/2004 | Zecha, Jr. et al. |
| 6,830,562 B2 | 12/2004 | Mogensen et al. |
| 6,837,877 B2 | 1/2005 | Zurcher et al. |
| 6,837,878 B2 | 1/2005 | Smutney et al. |
| 6,840,922 B2 | 1/2005 | Nielsen et al. |
| 6,880,701 B2 | 4/2005 | Bergeron et al. |
| 6,923,791 B2 | 8/2005 | Douglas |
| 6,926,694 B2 | 8/2005 | Marano-Ford et al. |
| 6,939,324 B2 | 9/2005 | Gonnelli et al. |
| 6,939,331 B2 | 9/2005 | Ohshima |
| 6,949,084 B2 | 9/2005 | Marggi et al. |
| 6,959,812 B2 | 11/2005 | Reif et al. |
| 6,960,193 B2 | 11/2005 | Rosenberg |
| 6,979,316 B1 | 12/2005 | Rubin et al. |
| 6,991,619 B2 | 1/2006 | Marano-Ford et al. |
| 6,991,620 B2 | 1/2006 | Marano-Ford et al. |
| 6,994,213 B2 | 2/2006 | Giard et al. |
| 6,997,907 B2 | 2/2006 | Safabash et al. |
| 7,014,625 B2 | 3/2006 | Bengtsson |
| 7,018,344 B2 | 3/2006 | Bressler et al. |
| 7,022,108 B2 | 4/2006 | Marano-Ford et al. |
| 7,047,070 B2 | 5/2006 | Wilkinson et al. |
| 7,052,483 B2 | 5/2006 | Wojcik |
| 7,055,713 B2 | 6/2006 | Rea et al. |
| 7,056,302 B2 | 6/2006 | Douglas |
| 7,070,580 B2 | 7/2006 | Nielsen |
| 7,074,208 B2 | 7/2006 | Pajunk et al. |
| D526,409 S | 8/2006 | Nielsen et al. |
| 7,083,592 B2 | 8/2006 | Lastovich et al. |
| 7,083,597 B2 | 8/2006 | Lynch et al. |
| 7,097,631 B2 | 8/2006 | Trautman et al. |
| 7,109,878 B2 | 9/2006 | Mann et al. |
| 7,115,108 B2 | 10/2006 | Wilkinson et al. |
| 7,115,112 B2 | 10/2006 | Mogensen et al. |
| 7,137,968 B1 | 11/2006 | Burrell et al. |
| 7,141,023 B2 | 11/2006 | Diermann et al. |
| 7,147,623 B2 | 12/2006 | Mathiasen |
| 7,186,236 B2 | 3/2007 | Gibson et al. |
| 7,211,068 B2 | 5/2007 | Douglas |
| 7,214,207 B2 | 5/2007 | Lynch et al. |
| 7,214,215 B2 | 5/2007 | Heinzerling et al. |
| 7,250,037 B2 | 7/2007 | Shermer et al. |
| 7,258,680 B2 | 8/2007 | Mogensen et al. |
| D554,253 S | 10/2007 | Kornerup |
| 7,303,543 B1 | 12/2007 | Maule et al. |
| 7,309,326 B2 | 12/2007 | Fangrow, Jr. et al. |
| 7,322,473 B2 | 1/2008 | Fux |
| 7,407,491 B2 | 8/2008 | Fangrow, Jr. et al. |
| 7,407,493 B2 | 8/2008 | Cane et al. |
| 7,431,876 B2 | 10/2008 | Mejlhede et al. |
| 7,441,655 B1 | 10/2008 | Hoftman |
| 7,569,262 B2 | 8/2009 | Szabo et al. |
| 7,648,494 B2 | 1/2010 | Kornerup et al. |
| 7,766,867 B2 | 8/2010 | Lynch et al. |
| 7,846,132 B2 | 12/2010 | Gravesen et al. |
| 7,850,652 B2 | 12/2010 | Liniger et al. |
| 8,012,126 B2 | 9/2011 | Tipsmark et al. |
| 8,087,333 B2 | 1/2012 | Oishi |
| 8,123,724 B2 | 2/2012 | Gillespie, III et al. |
| 8,303,549 B2 | 11/2012 | Mejlhede et al. |
| 8,323,250 B2 | 12/2012 | Chong et al. |
| 10,071,210 B2 | 9/2018 | Gray |
| 10,292,641 B2 | 5/2019 | Bureau et al. |
| 10,293,101 B2 | 5/2019 | Brewer et al. |
| 10,369,274 B2 | 8/2019 | O'Connor et al. |
| 10,369,289 B2 | 8/2019 | Cabiri et al. |
| 10,376,638 B2 | 8/2019 | Levesque et al. |
| 10,413,661 B2 | 9/2019 | Kamen et al. |
| 10,432,403 B2 | 10/2019 | Moskal |
| 10,434,245 B2 | 10/2019 | Yodfat et al. |
| 10,434,247 B2 | 10/2019 | Cole et al. |
| 10,434,253 B2 | 10/2019 | DiPema et al. |
| 10,434,285 B2 | 10/2019 | Schoonrnaker et al. |
| 10,438,696 B2 | 10/2019 | Shapley et al. |
| 10,441,356 B2 | 10/2019 | Zarins et al. |
| 10,441,718 B2 | 10/2019 | Tchao et al. |
| 10,441,723 B2 | 10/2019 | Nazzaro |
| 10,441,775 B2 | 10/2019 | Schriver et al. |
| 10,449,290 B2 | 10/2019 | Shapley et al. |
| 10,449,291 B2 | 10/2019 | Hadian et al. |
| 10,449,306 B2 | 10/2019 | Grover et al. |
| 10,463,785 B2 | 11/2019 | Dewey |
| 10,463,791 B2 | 11/2019 | Shergold et al. |
| 10,471,203 B2 | 11/2019 | Chappel et al. |
| 10,471,206 B2 | 11/2019 | Dittrich |
| 10,478,550 B2 | 11/2019 | Hadvary et al. |
| 10,478,552 B2 | 11/2019 | Cronenberg et al. |
| 10,478,554 B2 | 11/2019 | Bazargan et al. |
| 10,478,555 B2 | 11/2019 | Radojlcic |
| 10,483,000 B2 | 11/2019 | Saint et al. |
| 10,485,923 B2 | 11/2019 | Schiendzielorz |
| 10,485,937 B2 | 11/2019 | Yodfat et al. |
| 10,489,617 B2 | 11/2019 | Salem et al. |
| 10,493,201 B2 | 12/2019 | Cole et al. |
| 10,493,202 B2 | 12/2019 | Hayter |
| 10,493,203 B2 | 12/2019 | Yodfat et al. |
| 10,500,352 B2 | 12/2019 | Grant et al. |
| 10,507,316 B2 | 12/2019 | Fielder et al. |
| 10,512,724 B2 | 12/2019 | Renstad et al. |
| 10,525,193 B2 | 1/2020 | Schauderna |
| 10,525,247 B2 | 1/2020 | Bellrichard et al. |
| 10,532,150 B2 | 1/2020 | Bazargan et al. |
| 10,532,151 B2 | 1/2020 | Wei |
| 10,532,155 B2 | 1/2020 | Schiendzielorz |
| 10,532,159 B2 | 1/2020 | Tornsten et al. |
| 10,532,835 B2 | 1/2020 | Chong et al. |
| 10,537,681 B2 | 1/2020 | Tan-Malecki et al. |
| 10,539,481 B2 | 1/2020 | Piahey et al. |
| 10,542,936 B2 | 1/2020 | Goldberg et al. |
| 10,549,029 B2 | 2/2020 | Agard et al. |
| 10,549,033 B2 | 2/2020 | Shimizu |
| 10,549,034 B2 | 2/2020 | Eggert et al. |
| 10,549,036 B2 | 2/2020 | Starkweather et al. |
| 10,549,079 B2 | 2/2020 | Burton et al. |
| 10,556,059 B2 | 2/2020 | Cross et al. |
| 10,556,063 B2 | 2/2020 | Murphy, Jr. et al. |
| 10,561,785 B2 | 2/2020 | Roy et al. |
| 10,561,789 B2 | 2/2020 | Mastrototaro et al. |
| 10,561,825 B2 | 2/2020 | Amano et al. |
| 10,561,831 B2 | 2/2020 | Kato |
| 10,569,011 B2 | 2/2020 | Dilanni et al. |
| 10,569,012 B2 | 2/2020 | Schabbach et al. |
| 10,569,014 B2 | 2/2020 | Hanson et al. |
| 10,576,203 B2 | 3/2020 | Amon et al. |
| 10,576,204 B2 | 3/2020 | Estes et al. |
| 10,583,241 B2 | 3/2020 | Wu et al. |
| 10,583,247 B2 | 3/2020 | Mandro |

(56) References Cited

U.S. PATENT DOCUMENTS

| | | |
|---|---|---|
| 10,589,023 B2 | 3/2020 | Cindrich et al. |
| 10,589,028 B2 | 3/2020 | Cabiri et al. |
| 10,596,317 B2 | 3/2020 | Nakanishi |
| 10,596,362 B2 | 3/2020 | Fielder et al. |
| 10,610,638 B2 | 4/2020 | Cabiri et al. |
| 10,617,817 B2 | 4/2020 | Hwang et al. |
| 10,617,820 B2 | 4/2020 | O'Connor et al. |
| 10,625,016 B2 | 4/2020 | Amon et al. |
| 10,625,017 B2 | 4/2020 | Searle et al. |
| 10,625,018 B2 | 4/2020 | Destefano et al. |
| 10,632,248 B2 | 4/2020 | Stefanov et al. |
| 10,632,249 B2 | 4/2020 | Marbet et al. |
| 10,632,253 B2 | 4/2020 | Uchiyama et al. |
| 10,632,256 B2 | 4/2020 | Sasaki |
| 10,632,257 B2 | 4/2020 | Estes et al. |
| 10,635,784 B2 | 4/2020 | Rubalcaba, Jr. et al. |
| 10,639,418 B2 | 5/2020 | Kamen et al. |
| 10,639,661 B2 | 5/2020 | Fontana |
| 10,646,643 B2 | 5/2020 | Cabiri et al. |
| 10,646,652 B2 | 5/2020 | McCullough et al. |
| 10,646,653 B2 | 5/2020 | Despa et al. |
| 10,653,828 B2 | 5/2020 | Brown et al. |
| 10,653,829 B2 | 5/2020 | Barchen et al. |
| 10,653,833 B2 | 5/2020 | Kamen et al. |
| 10,653,835 B2 | 5/2020 | Dobbles et al. |
| 10,653,846 B2 | 5/2020 | Weibel et al. |
| 10,661,006 B2 | 5/2020 | Antonio et al. |
| 10,661,007 B2 | 5/2020 | Estes |
| 10,661,008 B2 | 5/2020 | Brewer et al. |
| 10,661,067 B2 | 5/2020 | Kodama |
| 10,668,210 B2 | 6/2020 | Kamen et al. |
| 10,668,213 B2 | 6/2020 | Cabiri |
| 10,668,227 B2 | 6/2020 | Caspers |
| 10,675,055 B2 | 6/2020 | Chong et al. |
| 10,675,333 B2 | 6/2020 | Ning et al. |
| 10,675,404 B2 | 6/2020 | Pizzochero et al. |
| 10,682,458 B2 | 6/2020 | Wu et al. |
| 10,682,460 B2 | 6/2020 | Adams et al. |
| 10,682,461 B2 | 6/2020 | Oakes |
| 10,682,463 B2 | 6/2020 | Kamen et al. |
| 10,685,749 B2 | 6/2020 | Hayter et al. |
| 10,688,241 B2 | 6/2020 | Yang |
| 10,688,243 B2 | 6/2020 | Cabiri |
| 10,688,294 B2 | 6/2020 | Cowan et al. |
| 10,716,891 B2 | 7/2020 | Saab et al. |
| 10,716,893 B2 | 7/2020 | Gray et al. |
| 10,716,895 B2 | 7/2020 | Brewer et al. |
| 10,716,896 B2 | 7/2020 | O'Connor et al. |
| 10,716,926 B2 | 7/2020 | Burton et al. |
| 10,719,584 B2 | 7/2020 | Drew |
| 10,722,643 B2 | 7/2020 | Gray et al. |
| 10,722,646 B2 | 7/2020 | Cole et al. |
| 10,722,647 B2 | 7/2020 | Gray |
| 10,722,650 B2 | 7/2020 | Duke et al. |
| 10,722,661 B2 | 7/2020 | Mandro et al. |
| 10,729,842 B2 | 8/2020 | Hooven et al. |
| 10,729,844 B2 | 8/2020 | Cole et al. |
| 10,737,015 B2 | 8/2020 | Estes |
| 10,737,016 B2 | 8/2020 | Smith et al. |
| 10,737,021 B2 | 8/2020 | Deck |
| 10,737,024 B2 | 8/2020 | Schmid |
| 10,737,026 B2 | 8/2020 | Teutsch |
| 10,737,038 B2 | 8/2020 | Cole et al. |
| 10,744,257 B2 | 8/2020 | Mandro et al. |
| 10,751,467 B2 | 8/2020 | Kamen et al. |
| 10,751,468 B2 | 8/2020 | Abal |
| 10,751,476 B2 | 8/2020 | Gazeley et al. |
| 10,757,219 B2 | 8/2020 | Moskal |
| 10,758,683 B2 | 9/2020 | Gibson et al. |
| 10,758,721 B2 | 9/2020 | Sonderegger et al. |
| 10,765,801 B2 | 9/2020 | McCullough |
| 10,765,803 B2 | 9/2020 | Gonnelli |
| 10,765,807 B2 | 9/2020 | Allis et al. |
| 10,772,796 B2 | 9/2020 | Kavazov |
| 10,773,019 B2 | 9/2020 | Searle et al. |
| 10,780,215 B2 | 9/2020 | Rosinko et al. |
| 10,780,216 B2 | 9/2020 | Farra |
| 10,780,220 B2 | 9/2020 | Gray |
| 10,780,223 B2 | 9/2020 | Desborough et al. |
| 10,792,419 B2 | 10/2020 | Kamen et al. |
| 10,792,424 B2 | 10/2020 | Sasaki |
| 10,792,440 B2 | 10/2020 | Mandro et al. |
| 10,799,630 B2 | 10/2020 | McCullough |
| 10,799,631 B2 | 10/2020 | Barmaimon et al. |
| 10,799,632 B2 | 10/2020 | Kohlbrecher |
| 10,806,851 B2 | 10/2020 | Rosinko |
| 10,806,854 B2 | 10/2020 | O'Connor et al. |
| 10,806,855 B2 | 10/2020 | Destefano et al. |
| 10,806,859 B2 | 10/2020 | Desborough et al. |
| 10,814,061 B2 | 10/2020 | Bene et al. |
| 11,110,261 B2 * | 9/2021 | Fruerlund ............ A61M 39/10 |
| 11,136,971 B2 | 10/2021 | Kamen et al. |
| 11,136,972 B2 | 10/2021 | Kamen et al. |
| 11,241,534 B2 | 2/2022 | Miller et al. |
| 11,261,858 B2 | 3/2022 | Kamen et al. |
| 11,293,425 B2 | 4/2022 | Kamen et al. |
| 11,339,774 B2 | 5/2022 | Gray et al. |
| 11,364,335 B2 | 6/2022 | Lanigan et al. |
| 11,386,482 B2 | 7/2022 | Estes |
| 11,391,273 B2 | 7/2022 | Kamen et al. |
| 2001/0004970 A1 | 6/2001 | Hollister et al. |
| 2001/0016714 A1 | 8/2001 | Bell et al. |
| 2001/0021827 A1 | 9/2001 | Ferguson et al. |
| 2001/0039387 A1 | 11/2001 | Rutynowski et al. |
| 2001/0039401 A1 | 11/2001 | Ferguson et al. |
| 2001/0041875 A1 | 11/2001 | Higuchi et al. |
| 2001/0049496 A1 | 12/2001 | Kirchhofer et al. |
| 2001/0053889 A1 | 12/2001 | Marggi et al. |
| 2001/0056284 A1 | 12/2001 | Purcell et al. |
| 2002/0022798 A1 | 2/2002 | Connelly et al. |
| 2002/0022855 A1 | 2/2002 | Bobroff et al. |
| 2002/0026152 A1 | 2/2002 | Bierman |
| 2002/0055711 A1 | 5/2002 | Lavi et al. |
| 2002/0068904 A1 | 6/2002 | Bierman et al. |
| 2002/0072720 A1 | 6/2002 | Hague et al. |
| 2002/0074345 A1 | 6/2002 | Schneider et al. |
| 2002/0077599 A1 | 6/2002 | Wojcik |
| 2002/0082543 A1 | 6/2002 | Park et al. |
| 2002/0095138 A1 | 7/2002 | Lynch et al. |
| 2002/0107489 A1 | 8/2002 | Lee |
| 2002/0111581 A1 | 8/2002 | Sasso |
| 2002/0156424 A1 | 10/2002 | Suzuki et al. |
| 2002/0156427 A1 | 10/2002 | Suzuki et al. |
| 2002/0161322 A1 | 10/2002 | Utterberg et al. |
| 2002/0161332 A1 | 10/2002 | Ramey |
| 2002/0161386 A1 | 10/2002 | Halseth et al. |
| 2002/0165493 A1 | 11/2002 | Bierman |
| 2002/0169419 A1 | 11/2002 | Steg |
| 2002/0173748 A1 | 11/2002 | McConnell et al. |
| 2002/0173769 A1 | 11/2002 | Gray et al. |
| 2002/0183688 A1 | 12/2002 | Lastovich et al. |
| 2002/0189688 A1 | 12/2002 | Roorda |
| 2002/0193737 A1 | 12/2002 | Popovsky |
| 2002/0193744 A1 | 12/2002 | Alesi et al. |
| 2003/0014018 A1 | 1/2003 | Giambattista et al. |
| 2003/0060781 A1 | 3/2003 | Mogensen et al. |
| 2003/0069548 A1 | 4/2003 | Connelly et al. |
| 2003/0088238 A1 | 5/2003 | Poulsen et al. |
| 2003/0109829 A1 | 6/2003 | Mogensen et al. |
| 2003/0125669 A1 | 7/2003 | Safabash et al. |
| 2003/0125678 A1 | 7/2003 | Swenson et al. |
| 2003/0130619 A1 | 7/2003 | Safabash et al. |
| 2003/0139704 A1 | 7/2003 | Lin |
| 2003/0158520 A1 | 8/2003 | Safabash et al. |
| 2003/0176843 A1 | 9/2003 | Wilkinson |
| 2003/0176852 A1 | 9/2003 | Lynch et al. |
| 2003/0181863 A1 | 9/2003 | Ackley et al. |
| 2003/0181868 A1 | 9/2003 | Swenson |
| 2003/0181873 A1 | 9/2003 | Swenson |
| 2003/0181874 A1 | 9/2003 | Bressler et al. |
| 2003/0187394 A1 | 10/2003 | Wilkinson et al. |
| 2003/0187395 A1 | 10/2003 | Gabel et al. |
| 2003/0199823 A1 | 10/2003 | Bobroff et al. |
| 2003/0216686 A1 | 11/2003 | Lynch et al. |

(56) References Cited

U.S. PATENT DOCUMENTS

| | | |
|---|---|---|
| 2003/0220610 A1 | 11/2003 | Lastovich et al. |
| 2003/0225373 A1 | 12/2003 | Bobroff et al. |
| 2003/0225374 A1 | 12/2003 | Mathiasen |
| 2003/0229308 A1 | 12/2003 | Tsals et al. |
| 2003/0229316 A1 | 12/2003 | Hwang et al. |
| 2004/0002682 A1 | 1/2004 | Kovelman et al. |
| 2004/0006316 A1 | 1/2004 | Patton |
| 2004/0044306 A1 | 3/2004 | Lynch et al. |
| 2004/0049159 A1 | 3/2004 | Barrus et al. |
| 2004/0055711 A1 | 3/2004 | Martin et al. |
| 2004/0059316 A1 | 3/2004 | Smedegaard |
| 2004/0068231 A1 | 4/2004 | Blondeau |
| 2004/0069044 A1 | 4/2004 | Lavi et al. |
| 2004/0087913 A1 | 5/2004 | Rogers et al. |
| 2004/0092865 A1 | 5/2004 | Flaherty et al. |
| 2004/0092875 A1 | 5/2004 | Kochamba |
| 2004/0111068 A1 | 6/2004 | Swenson |
| 2004/0112781 A1 | 6/2004 | Hofverberg et al. |
| 2004/0116865 A1 | 6/2004 | Bengtsson |
| 2004/0133164 A1 | 7/2004 | Funderburk et al. |
| 2004/0138612 A1 | 7/2004 | Shermer et al. |
| 2004/0138620 A1 | 7/2004 | Douglas et al. |
| 2004/0143216 A1 | 7/2004 | Douglas et al. |
| 2004/0143218 A1 | 7/2004 | Das |
| 2004/0158202 A1 | 8/2004 | Jensen |
| 2004/0158207 A1 | 8/2004 | Hunn et al. |
| 2004/0162518 A1 | 8/2004 | Connelly et al. |
| 2004/0162521 A1 | 8/2004 | Bengtsson |
| 2004/0171989 A1 | 9/2004 | Horner et al. |
| 2004/0178098 A1 | 9/2004 | Swenson et al. |
| 2004/0186446 A1 | 9/2004 | Ohshima |
| 2004/0193143 A1 | 9/2004 | Sauer |
| 2004/0199123 A1 | 10/2004 | Nielsen |
| 2004/0204673 A1 | 10/2004 | Flaherty |
| 2004/0204687 A1 | 10/2004 | Mogensen et al. |
| 2004/0204690 A1 | 10/2004 | Yashiro et al. |
| 2004/0215151 A1 | 10/2004 | Marshall et al. |
| 2004/0220528 A1 | 11/2004 | Garcia et al. |
| 2004/0236284 A1 | 11/2004 | Hoste et al. |
| 2004/0238392 A1 | 12/2004 | Peterson et al. |
| 2004/0243065 A1 | 12/2004 | McConnell et al. |
| 2004/0254433 A1 | 12/2004 | Bandis et al. |
| 2004/0260235 A1 | 12/2004 | Douglas |
| 2004/0260250 A1 | 12/2004 | Harris et al. |
| 2005/0035014 A1 | 2/2005 | Cane et al. |
| 2005/0038378 A1 | 2/2005 | Lastovich et al. |
| 2005/0043687 A1 | 2/2005 | Mogensen et al. |
| 2005/0049571 A1 | 3/2005 | Lastovich et al. |
| 2005/0065466 A1 | 3/2005 | Vedrine |
| 2005/0065472 A1 | 3/2005 | Cindrich et al. |
| 2005/0075606 A1 | 4/2005 | Botich et al. |
| 2005/0080386 A1 | 4/2005 | Reid |
| 2005/0101910 A1 | 5/2005 | Bowman et al. |
| 2005/0101912 A1 | 5/2005 | Faust et al. |
| 2005/0101933 A1 | 5/2005 | Marrs et al. |
| 2005/0107743 A1 | 5/2005 | Fangrow, Jr. et al. |
| 2005/0113761 A1 | 5/2005 | Faust et al. |
| 2005/0119611 A1 | 6/2005 | Marano-Ford et al. |
| 2005/0119619 A1 | 6/2005 | Haining |
| 2005/0119637 A1 | 6/2005 | Lundgren et al. |
| 2005/0124936 A1 | 6/2005 | Mogensen et al. |
| 2005/0131347 A1 | 6/2005 | Marano-Ford et al. |
| 2005/0159709 A1 | 7/2005 | Wilkinson |
| 2005/0159714 A1 | 7/2005 | Gibson et al. |
| 2005/0165382 A1 | 7/2005 | Fulford |
| 2005/0173044 A1 | 8/2005 | Drummond |
| 2005/0192560 A1 | 9/2005 | Walls et al. |
| 2005/0203461 A1 | 9/2005 | Flaherty et al. |
| 2005/0215979 A1 | 9/2005 | Kornerup et al. |
| 2005/0240154 A1 | 10/2005 | Mogensen et al. |
| 2005/0251098 A1 | 11/2005 | Wyss et al. |
| 2005/0256456 A1 | 11/2005 | Marano-Ford et al. |
| 2005/0261629 A1 | 11/2005 | Marano-Ford et al. |
| 2005/0277892 A1 | 12/2005 | Chen |
| 2005/0283114 A1 | 12/2005 | Bresina et al. |
| 2006/0015063 A1 | 1/2006 | Buetikofer et al. |
| 2006/0015076 A1 | 1/2006 | Keinzerling et al. |
| 2006/0030815 A1 | 2/2006 | Csincsura et al. |
| 2006/0036214 A1 | 2/2006 | Mogensen et al. |
| 2006/0041224 A1 | 2/2006 | Jensen et al. |
| 2006/0069351 A9 | 3/2006 | Safabash et al. |
| 2006/0069382 A1 | 3/2006 | Pedersen |
| 2006/0069383 A1 | 3/2006 | Bogaerts et al. |
| 2006/0095003 A1 | 5/2006 | Marano-Ford et al. |
| 2006/0095014 A1 | 5/2006 | Ethelfeld et al. |
| 2006/0102550 A1 | 5/2006 | Joseph et al. |
| 2006/0106346 A1 | 5/2006 | Sullivan et al. |
| 2006/0129123 A1 | 6/2006 | Wojcik |
| 2006/0135908 A1 | 6/2006 | Liniger et al. |
| 2006/0135913 A1 | 6/2006 | Ethelfeld et al. |
| 2006/0142698 A1 | 6/2006 | Ethelfeld et al. |
| 2006/0161108 A1 | 7/2006 | Mogensen et al. |
| 2006/0173410 A1 | 8/2006 | Moberg et al. |
| 2006/0173413 A1 | 8/2006 | Fan |
| 2006/0184104 A1 | 8/2006 | Cheney et al. |
| 2006/0184140 A1 | 8/2006 | Okiyama |
| 2006/0200073 A1 | 9/2006 | Radmer et al. |
| 2006/0241551 A1 | 10/2006 | Lynch et al. |
| 2006/0247553 A1 | 11/2006 | Diermann et al. |
| 2006/0247574 A1 | 11/2006 | Maule et al. |
| 2006/0253085 A1 | 11/2006 | Geismar et al. |
| 2006/0253086 A1 | 11/2006 | Moberg et al. |
| 2006/0264835 A1 | 11/2006 | Nielsen et al. |
| 2006/0264890 A1 | 11/2006 | Moberg et al. |
| 2007/0005017 A1 | 1/2007 | Alohas et al. |
| 2007/0016129 A1 | 1/2007 | Liniger et al. |
| 2007/0016159 A1 | 1/2007 | Sparholt et al. |
| 2007/0021729 A1 | 1/2007 | Mogensen et al. |
| 2007/0049865 A1 | 3/2007 | Radmer et al. |
| 2007/0049870 A1 | 3/2007 | Gray et al. |
| 2007/0051784 A1 | 3/2007 | Money et al. |
| 2007/0066955 A1 | 3/2007 | Sparholt et al. |
| 2007/0066958 A1 | 3/2007 | Wright |
| 2007/0088271 A1 | 4/2007 | Richards |
| 2007/0093754 A1 | 4/2007 | Mogensen et al. |
| 2007/0104596 A1 | 5/2007 | Preuthun et al. |
| 2007/0106244 A1 | 5/2007 | Mosler et al. |
| 2007/0112301 A1 | 5/2007 | Preuthun et al. |
| 2007/0112303 A1 | 5/2007 | Liniger et al. |
| 2007/0124002 A1 | 5/2007 | Estes et al. |
| 2007/0129688 A1 | 6/2007 | Scheurer et al. |
| 2007/0129691 A1 | 6/2007 | Sage, Jr. et al. |
| 2007/0173767 A1 | 7/2007 | Lynch et al. |
| 2007/0179444 A1 | 8/2007 | Causey et al. |
| 2007/0185441 A1 | 8/2007 | Fangrow, Jr. et al. |
| 2007/0191770 A1 | 8/2007 | Moberg et al. |
| 2007/0191772 A1 | 8/2007 | Wojcik |
| 2007/0191773 A1 | 8/2007 | Wojcik |
| 2007/0203454 A1 | 8/2007 | Shermer et al. |
| 2007/0213673 A1 | 9/2007 | Douglas |
| 2007/0219480 A1 | 9/2007 | Kamen et al. |
| 2007/0244448 A1 | 10/2007 | Lastovich et al. |
| 2007/0282269 A1 | 12/2007 | Carter et al. |
| 2007/0299409 A1 | 12/2007 | Whitbourne et al. |
| 2008/0058692 A1 | 3/2008 | Propp et al. |
| 2008/0119707 A1 | 5/2008 | Stafford |
| 2008/0200897 A1 | 8/2008 | Hoss et al. |
| 2008/0215035 A1 | 9/2008 | Yodfat et al. |
| 2008/0234630 A1 | 9/2008 | Iddan et al. |
| 2008/0269687 A1 | 10/2008 | Chong et al. |
| 2008/0290657 A1 | 11/2008 | McKeon, III |
| 2008/0312601 A1 | 12/2008 | Cane |
| 2009/0062767 A1 | 3/2009 | Van et al. |
| 2009/0118592 A1 | 5/2009 | Klitgaard |
| 2009/0196675 A1 | 8/2009 | Mey et al. |
| 2009/0326453 A1 | 12/2009 | Adams et al. |
| 2009/0326456 A1 | 12/2009 | Cross et al. |
| 2010/0004597 A1 | 1/2010 | Gyrn et al. |
| 2010/0022956 A1 | 1/2010 | Tipsmark et al. |
| 2010/0049128 A1 | 2/2010 | McKenzie et al. |
| 2010/0094251 A1 | 4/2010 | Estes |
| 2010/0135831 A1 | 6/2010 | Jacobsen |
| 2010/0137829 A1 | 6/2010 | Nielsen et al. |
| 2010/0145303 A1 | 6/2010 | Yodfat et al. |

(56) References Cited

U.S. PATENT DOCUMENTS

| | | |
|---|---|---|
| 2010/0168670 A1 | 7/2010 | Srlsathapat et al. |
| 2010/0228226 A1 | 9/2010 | Nielsen |
| 2010/0241103 A1 | 9/2010 | Kraft et al. |
| 2010/0262078 A1 | 10/2010 | Blomquist |
| 2011/0040247 A1 | 2/2011 | Mandro et al. |
| 2011/0054399 A1 | 3/2011 | Chong et al. |
| 2011/0112484 A1 | 5/2011 | Carter et al. |
| 2011/0112696 A1 | 5/2011 | Yodfat et al. |
| 2011/0118578 A1 | 5/2011 | Timmerman |
| 2011/0160652 A1 | 6/2011 | Yodfat et al. |
| 2011/0160666 A1 | 6/2011 | Hanson et al. |
| 2011/0190704 A1* | 8/2011 | Lynch .................. A61M 5/145 604/152 |
| 2011/0313357 A1 | 12/2011 | Skutnik et al. |
| 2012/0078170 A1 | 3/2012 | Smith et al. |
| 2012/0136300 A1 | 5/2012 | Schoonrnaker et al. |
| 2012/0150123 A1 | 6/2012 | Lawrence et al. |
| 2012/0209085 A1 | 8/2012 | Degen et al. |
| 2012/0238851 A1 | 9/2012 | Kamen et al. |
| 2013/0046239 A1 | 2/2013 | Gonnelli et al. |
| 2013/0046508 A1 | 2/2013 | Sur et al. |
| 2013/0053823 A1 | 2/2013 | Fiering et al. |
| 2013/0060233 A1 | 3/2013 | O'Connor et al. |
| 2013/0138075 A1 | 5/2013 | Lambert |
| 2013/0226138 A1 | 8/2013 | Sia |
| 2013/0237955 A1 | 9/2013 | Neta et al. |
| 2014/0025002 A1 | 1/2014 | Qi et al. |
| 2014/0031793 A1 | 1/2014 | Constantineau et al. |
| 2014/0052096 A1 | 2/2014 | Searle et al. |
| 2014/0054883 A1 | 2/2014 | Lanigan et al. |
| 2014/0127048 A1 | 5/2014 | Dilanni et al. |
| 2014/0128815 A1 | 5/2014 | Cabiri et al. |
| 2014/0276379 A1 | 9/2014 | Uram et al. |
| 2014/0276536 A1 | 9/2014 | Estes |
| 2014/0323961 A1 | 10/2014 | Blomquist et al. |
| 2014/0358112 A1 | 12/2014 | Smith et al. |
| 2015/0025503 A1 | 1/2015 | Searle et al. |
| 2015/0073384 A1 | 3/2015 | Limaye |
| 2015/0080799 A1 | 3/2015 | Schneider et al. |
| 2015/0080800 A1 | 3/2015 | Cronenberg |
| 2015/0105720 A1 | 4/2015 | Montalvo et al. |
| 2015/0112269 A1 | 4/2015 | Sumida et al. |
| 2015/0209505 A1 | 7/2015 | Hanson et al. |
| 2015/0273201 A1 | 10/2015 | Tallarida et al. |
| 2015/0314117 A1 | 11/2015 | Arami et al. |
| 2016/0051750 A1 | 2/2016 | Tsoukalis |
| 2016/0074578 A1 | 3/2016 | Xu et al. |
| 2016/0082182 A1 | 3/2016 | Gregory et al. |
| 2016/0089056 A1 | 3/2016 | Limaye et al. |
| 2016/0089524 A1 | 3/2016 | Anderson |
| 2016/0144105 A1 | 5/2016 | Hooven et al. |
| 2016/0193407 A1 | 7/2016 | Qin et al. |
| 2016/0346469 A1 | 12/2016 | Shubinsky et al. |
| 2017/0080157 A1 | 3/2017 | Cabiri et al. |
| 2017/0100542 A1 | 4/2017 | Norton et al. |
| 2017/0232191 A1 | 8/2017 | Smith et al. |
| 2017/0258987 A1 | 9/2017 | Caspers |
| 2017/0290971 A1 | 10/2017 | Hedmann et al. |
| 2017/0296741 A1 | 10/2017 | Gregory |
| 2017/0296742 A1 | 10/2017 | Stefanov |
| 2017/0340827 A1 | 11/2017 | Nazzaro et al. |
| 2017/0340841 A1 | 11/2017 | Sasaki |
| 2017/0351841 A1 | 12/2017 | Moskal |
| 2017/0351851 A1 | 12/2017 | Wang et al. |
| 2017/0368260 A1 | 12/2017 | McCullough et al. |
| 2018/0008768 A1 | 1/2018 | Prescher et al. |
| 2018/0028744 A1 | 2/2018 | Kim |
| 2018/0036476 A1 | 2/2018 | McCullough et al. |
| 2018/0071450 A1 | 3/2018 | Rullland |
| 2018/0110420 A1 | 4/2018 | Pekander |
| 2018/0185573 A1 | 7/2018 | Niklaus |
| 2018/0221571 A1 | 8/2018 | Carbone et al. |
| 2018/0344926 A1 | 12/2018 | Brandenburg et al. |
| 2018/0361061 A1 | 12/2018 | Andretta |
| 2018/0372085 A1 | 12/2018 | Veischow et al. |
| 2019/0009022 A1 | 1/2019 | Oakes |
| 2019/0083057 A1 | 3/2019 | Saul et al. |
| 2019/0175828 A1 | 6/2019 | List et al. |
| 2019/0262535 A1 | 8/2019 | Shubinsky et al. |
| 2019/0298485 A1 | 10/2019 | Forsell |
| 2019/0298912 A1 | 10/2019 | Spencer et al. |
| 2019/0298914 A1 | 10/2019 | Kamen et al. |
| 2019/0298918 A1 | 10/2019 | Jallon |
| 2019/0298921 A1 | 10/2019 | Stafford |
| 2019/0298925 A1 | 10/2019 | Cowe et al. |
| 2019/0307943 A1 | 10/2019 | Franano et al. |
| 2019/0307955 A1 | 10/2019 | Levesque et al. |
| 2019/0307970 A1 | 10/2019 | Kamen et al. |
| 2019/0321545 A1 | 10/2019 | Saint |
| 2019/0321552 A1 | 10/2019 | DiPerna et al. |
| 2019/0336678 A1 | 11/2019 | Rule |
| 2019/0336681 A1 | 11/2019 | Kamen et al. |
| 2019/0343434 A1 | 11/2019 | Varsavsky et al. |
| 2019/0344010 A1 | 11/2019 | Pizzochero et al. |
| 2019/0350501 A1 | 11/2019 | Blomquist et al. |
| 2019/0351134 A1 | 11/2019 | Cook et al. |
| 2019/0351209 A1 | 11/2019 | Butziger et al. |
| 2019/0358395 A1 | 11/2019 | Olson et al. |
| 2019/0358437 A1 | 11/2019 | Schwartz et al. |
| 2019/0366012 A1 | 12/2019 | Gross et al. |
| 2019/0368484 A1 | 12/2019 | Chappel et al. |
| 2019/0374709 A1 | 12/2019 | Cole et al. |
| 2019/0374714 A1 | 12/2019 | Rioux et al. |
| 2019/0374719 A1 | 12/2019 | Cabiri et al. |
| 2019/0374757 A1 | 12/2019 | Verhoeven et al. |
| 2019/0381241 A1 | 12/2019 | Bryant et al. |
| 2019/0388609 A1 | 12/2019 | Lanigan et al. |
| 2019/0388614 A1 | 12/2019 | Gyrn et al. |
| 2019/0388615 A1 | 12/2019 | Sonderegger et al. |
| 2020/0001005 A1 | 1/2020 | Politis et al. |
| 2020/0001006 A1 | 1/2020 | Pizzochero et al. |
| 2020/0001007 A1 | 1/2020 | Miesel et al. |
| 2020/0009317 A1 | 1/2020 | Cronenberg et al. |
| 2020/0009318 A1 | 1/2020 | Kamen et al. |
| 2020/0009319 A1 | 1/2020 | Ludolph |
| 2020/0009331 A1 | 1/2020 | Kamen et al. |
| 2020/0016329 A1 | 1/2020 | Schabbach et al. |
| 2020/0016333 A1 | 1/2020 | Soares et al. |
| 2020/0016335 A1 | 1/2020 | DiPerna et al. |
| 2020/0023121 A1 | 1/2020 | Thomas et al. |
| 2020/0023129 A1 | 1/2020 | Day et al. |
| 2020/0030528 A1 | 1/2020 | Burke et al. |
| 2020/0030531 A1 | 1/2020 | Day et al. |
| 2020/0030532 A1 | 1/2020 | Day et al. |
| 2020/0030533 A1 | 1/2020 | Day et al. |
| 2020/0030592 A1 | 1/2020 | Cheche |
| 2020/0038588 A1 | 2/2020 | Varsavsky et al. |
| 2020/0054822 A1 | 2/2020 | Dewey |
| 2020/0054825 A1 | 2/2020 | Kamen et al. |
| 2020/0054826 A1 | 2/2020 | Diianni et al. |
| 2020/0061287 A1 | 2/2020 | Chappel et al. |
| 2020/0069865 A1 | 3/2020 | Day et al. |
| 2020/0069869 A1 | 3/2020 | Grant et al. |
| 2020/0077340 A1 | 3/2020 | Kruse |
| 2020/0077948 A1 | 3/2020 | Schmid |
| 2020/0078511 A1 | 3/2020 | Focht et al. |
| 2020/0078513 A1 | 3/2020 | Wei |
| 2020/0086042 A1 | 3/2020 | Kamen et al. |
| 2020/0086043 A1 | 3/2020 | Saint |
| 2020/0101218 A1 | 4/2020 | Shapley et al. |
| 2020/0101226 A1 | 4/2020 | Rosinko et al. |
| 2020/0114069 A1 | 4/2020 | Searle et al. |
| 2020/0118676 A1 | 4/2020 | Spohn et al. |
| 2020/0121854 A1 | 4/2020 | Norton et al. |
| 2020/0121937 A1 | 4/2020 | Yoder et al. |
| 2020/0129692 A1 | 4/2020 | Kim et al. |
| 2020/0138852 A1 | 5/2020 | Chattaraj et al. |
| 2020/0138911 A1 | 5/2020 | Joseph et al. |
| 2020/0147304 A1 | 5/2020 | Crouther et al. |
| 2020/0147305 A1 | 5/2020 | Estes |
| 2020/0147309 A1 | 5/2020 | Quinn et al. |
| 2020/0164159 A1 | 5/2020 | Chattaraj et al. |
| 2020/0168316 A1 | 5/2020 | Kamen |
| 2020/0171236 A1 | 6/2020 | McCullough et al. |

(56) References Cited

U.S. PATENT DOCUMENTS

| | | |
|---|---|---|
| 2020/0179592 A1 | 6/2020 | Adams et al. |
| 2020/0179594 A1 | 6/2020 | Yodfat et al. |
| 2020/0179602 A1 | 6/2020 | Maziish |
| 2020/0179603 A1 | 6/2020 | Rosinko |
| 2020/0188580 A1 | 6/2020 | Gregory et al. |
| 2020/0188581 A1 | 6/2020 | Diianni et al. |
| 2020/0188588 A1 | 6/2020 | Estes |
| 2020/0197600 A1 | 6/2020 | Chow et al. |
| 2020/0197621 A1 | 6/2020 | Quinn et al. |
| 2020/0206418 A1 | 7/2020 | Gonnelli et al. |
| 2020/0215264 A1 | 7/2020 | Searle et al. |
| 2020/0215273 A1 | 7/2020 | Gibson et al. |
| 2020/0222624 A1 | 7/2020 | Destefano et al. |
| 2020/0222625 A1 | 7/2020 | Cabiri et al. |
| 2020/0230314 A1 | 7/2020 | Kondo et al. |
| 2020/0246541 A1 | 8/2020 | Neftel et al. |
| 2020/0253632 A1 | 8/2020 | Chong et al. |
| 2020/0254174 A1 | 8/2020 | Kruse et al. |
| 2020/0261002 A1 | 8/2020 | Pace |
| 2020/0261645 A1 | 8/2020 | Kamen et al. |
| 2020/0268962 A1 | 8/2020 | Gamelin |
| 2020/0268975 A1 | 8/2020 | Kim et al. |
| 2020/0272310 A1 | 8/2020 | Vik et al. |
| 2020/0276386 A1 | 9/2020 | Kamen et al. |
| 2020/0306446 A1 | 10/2020 | Kamen et al. |
| 2020/0306448 A1 | 10/2020 | Schmid |
| 2020/0316291 A1 | 10/2020 | Gibson et al. |
| 2020/0321094 A1 | 10/2020 | Saint et al. |
| 2020/0324048 A1 | 10/2020 | O'Connor et al. |
| 2020/0324101 A1 | 10/2020 | Hartmann et al. |
| 2020/0330679 A1 | 10/2020 | Cronenberg et al. |
| 2020/0330680 A1 | 10/2020 | Deck |
| 2020/0330701 A1 | 10/2020 | Cole et al. |
| 2020/0335194 A1 | 10/2020 | Jacobson et al. |
| 2020/0338257 A1 | 10/2020 | Hooven et al. |
| 2020/0338262 A1 | 10/2020 | Kamen et al. |
| 2020/0338264 A1 | 10/2020 | Allis et al. |
| 2020/0338266 A1 | 10/2020 | Estes |
| 2021/0060241 A1 | 3/2021 | Kamen et al. |
| 2021/0180583 A1 | 6/2021 | Gray |
| 2021/0180584 A1 | 6/2021 | Kamen et al. |
| 2021/0190063 A1 | 6/2021 | Gray |
| 2021/0196885 A1 | 7/2021 | Smith et al. |
| 2021/0268174 A1 | 9/2021 | Estes et al. |
| 2021/0270255 A1 | 9/2021 | Gray |
| 2021/0293232 A1 | 9/2021 | Kamen et al. |
| 2021/0393870 A1 | 12/2021 | Kessel et al. |
| 2021/0393939 A1 | 12/2021 | Lanigan et al. |
| 2021/0396221 A1 | 12/2021 | Kamen et al. |

FOREIGN PATENT DOCUMENTS

| | | |
|---|---|---|
| DE | 19631921 A1 | 3/1997 |
| DE | 29905072 U1 | 9/1999 |
| DE | 20320207 U1 | 10/2004 |
| EP | 0081655 A1 | 6/1983 |
| EP | 0272530 A2 | 6/1988 |
| EP | 0117632 B1 | 8/1989 |
| EP | 0239244 B1 | 9/1991 |
| EP | 0451040 A1 | 10/1991 |
| EP | 0615768 A2 | 9/1994 |
| EP | 0652027 A1 | 5/1995 |
| EP | 0657184 A1 | 6/1995 |
| EP | 0744183 A2 | 11/1996 |
| EP | 0747006 A1 | 12/1996 |
| EP | 0799626 A1 | 10/1997 |
| EP | 0544837 B1 | 11/1997 |
| EP | 0688232 B1 | 12/1998 |
| EP | 0937475 A2 | 8/1999 |
| EP | 0651662 B1 | 9/1999 |
| EP | 0956879 A1 | 11/1999 |
| EP | 1086718 A1 | 3/2001 |
| EP | 1125593 A1 | 8/2001 |
| EP | 0775501 B1 | 6/2002 |
| EP | 0714631 B1 | 12/2002 |
| EP | 1350537 A1 | 10/2003 |
| EP | 1360970 A1 | 11/2003 |
| EP | 1380315 A1 | 1/2004 |
| EP | 1407747 A1 | 4/2004 |
| EP | 1407793 A1 | 4/2004 |
| EP | 1421968 A2 | 5/2004 |
| EP | 1177802 B1 | 9/2004 |
| EP | 1329233 B1 | 9/2004 |
| EP | 1475113 A1 | 11/2004 |
| EP | 1495775 A1 | 1/2005 |
| EP | 1502613 A1 | 2/2005 |
| EP | 1525873 A1 | 4/2005 |
| EP | 1527792 A1 | 5/2005 |
| EP | 1559442 A2 | 8/2005 |
| EP | 1616594 A1 | 1/2006 |
| EP | 1704889 A1 | 9/2006 |
| EP | 1719537 A2 | 11/2006 |
| EP | 1762259 A1 | 3/2007 |
| EP | 1764125 A1 | 3/2007 |
| EP | 1776980 A1 | 4/2007 |
| EP | 1970091 A1 | 9/2008 |
| EP | 2075024 A1 | 7/2009 |
| EP | 2153865 A2 | 2/2010 |
| EP | 2272559 A1 | 1/2011 |
| EP | 3662967 B1 | 11/2021 |
| EP | 3988147 A1 | 4/2022 |
| FR | 2725902 A1 | 4/1996 |
| FR | 2752164 A1 | 2/1998 |
| GB | 2088215 A | 6/1982 |
| GB | 2230702 A | 10/1990 |
| GB | 2423267 A | 8/2006 |
| GB | 2450872 A | 1/2009 |
| GB | 2459101 A | 10/2009 |
| JP | H03191965 A | 8/1991 |
| JP | H0751251 A | 2/1995 |
| JP | H08187286 A | 7/1996 |
| JP | H10179734 A | 7/1998 |
| JP | 2002028246 A | 1/2002 |
| RU | 2238111 C2 | 10/2004 |
| SU | 933100 A1 | 6/1982 |
| WO | 8101795 A1 | 7/1981 |
| WO | 8203558 A1 | 10/1982 |
| WO | 9204062 A1 | 3/1992 |
| WO | 9305840 A2 | 4/1993 |
| WO | 9311709 A1 | 6/1993 |
| WO | 9420160 A1 | 9/1994 |
| WO | 9519194 A1 | 7/1995 |
| WO | 9620021 A1 | 7/1996 |
| WO | 9632981 A1 | 10/1996 |
| WO | 9826835 A1 | 6/1998 |
| WO | 9833549 A1 | 8/1998 |
| WO | 9858693 A1 | 12/1998 |
| WO | 9907435 A1 | 2/1999 |
| WO | 9922789 A1 | 5/1999 |
| WO | 9933504 A1 | 7/1999 |
| WO | 0002614 A1 | 1/2000 |
| WO | 0003757 A1 | 1/2000 |
| WO | 0044324 A1 | 8/2000 |
| WO | 0112746 A1 | 2/2001 |
| WO | 0130419 A2 | 5/2001 |
| WO | 0168180 A1 | 9/2001 |
| WO | 0172353 A2 | 10/2001 |
| WO | 0176684 A1 | 10/2001 |
| WO | 0193926 A2 | 12/2001 |
| WO | 0202165 A2 | 1/2002 |
| WO | 0207804 A1 | 1/2002 |
| WO | 0240083 A2 | 5/2002 |
| WO | 02053220 A2 | 7/2002 |
| WO | 02068014 A2 | 9/2002 |
| WO | 02081012 A2 | 10/2002 |
| WO | 02081013 A2 | 10/2002 |
| WO | 02083206 A2 | 10/2002 |
| WO | 02083228 A2 | 10/2002 |
| WO | 02094352 A2 | 11/2002 |
| WO | 02100457 A2 | 12/2002 |
| WO | 02102442 A1 | 12/2002 |
| WO | 03015860 A1 | 2/2003 |
| WO | 03026728 A1 | 4/2003 |
| WO | 03068305 A1 | 8/2003 |

(56) References Cited

FOREIGN PATENT DOCUMENTS

| | | |
|---|---|---|
| WO | 03075980 A2 | 9/2003 |
| WO | 03095003 A1 | 11/2003 |
| WO | 2004012796 A1 | 2/2004 |
| WO | 2004024219 A1 | 3/2004 |
| WO | 2004026375 A1 | 4/2004 |
| WO | 2004029457 A1 | 4/2004 |
| WO | 2004030726 A1 | 4/2004 |
| WO | 2004037325 A1 | 5/2004 |
| WO | 2004054644 A1 | 7/2004 |
| WO | 2004056412 A2 | 7/2004 |
| WO | 2004064593 A2 | 8/2004 |
| WO | 2004071308 A1 | 8/2004 |
| WO | 2004087240 A1 | 10/2004 |
| WO | 2004098683 A1 | 11/2004 |
| WO | 2004101016 A1 | 11/2004 |
| WO | 2004101071 A2 | 11/2004 |
| WO | 2004110527 A1 | 12/2004 |
| WO | 2005002649 A1 | 1/2005 |
| WO | 2005004973 A1 | 1/2005 |
| WO | 2005018703 A2 | 3/2005 |
| WO | 2005037184 A2 | 4/2005 |
| WO | 2005037350 A2 | 4/2005 |
| WO | 2005039673 A2 | 5/2005 |
| WO | 2005046780 A1 | 5/2005 |
| WO | 2005065748 A1 | 7/2005 |
| WO | 2005068006 A1 | 7/2005 |
| WO | 2005072795 A2 | 8/2005 |
| WO | 2005092410 A1 | 10/2005 |
| WO | 2005094920 A1 | 10/2005 |
| WO | 2005112800 A2 | 12/2005 |
| WO | 2005118055 A1 | 12/2005 |
| WO | 2006003130 A1 | 1/2006 |
| WO | 2006015507 A2 | 2/2006 |
| WO | 2006015600 A2 | 2/2006 |
| WO | 2006024650 A2 | 3/2006 |
| WO | 2006032689 A1 | 3/2006 |
| WO | 2006032692 A1 | 3/2006 |
| WO | 2006061027 A2 | 6/2006 |
| WO | 2006061354 A1 | 6/2006 |
| WO | 2006062680 A1 | 6/2006 |
| WO | 2006062912 A1 | 6/2006 |
| WO | 2006075016 A1 | 7/2006 |
| WO | 2006077262 A1 | 7/2006 |
| WO | 2006077263 A1 | 7/2006 |
| WO | 2006089958 A1 | 8/2006 |
| WO | 2006097111 A2 | 9/2006 |
| WO | 2006108775 A2 | 10/2006 |
| WO | 2006120253 A2 | 11/2006 |
| WO | 2006121921 A2 | 11/2006 |
| WO | 2006122048 A1 | 11/2006 |
| WO | 2007000162 A2 | 1/2007 |
| WO | 2007002523 A2 | 1/2007 |
| WO | 2007020090 A1 | 2/2007 |
| WO | 2007065944 A1 | 6/2007 |
| WO | 2007071255 A1 | 6/2007 |
| WO | 2007071258 A1 | 6/2007 |
| WO | 2007093051 A1 | 8/2007 |
| WO | 2007093182 A2 | 8/2007 |
| WO | 2007122207 A1 | 11/2007 |
| WO | 2007140631 A1 | 12/2007 |
| WO | 2007140783 A2 | 12/2007 |
| WO | 2007140785 A1 | 12/2007 |
| WO | 2007141210 A1 | 12/2007 |
| WO | 2008014791 A1 | 2/2008 |
| WO | 2008014792 A1 | 2/2008 |
| WO | 2008048631 A1 | 4/2008 |
| WO | 2008052545 A1 | 5/2008 |
| WO | 2008057958 A2 | 5/2008 |
| WO | 2008058133 A2 | 5/2008 |
| WO | 2008065646 A1 | 6/2008 |
| WO | 2008092782 A1 | 8/2008 |
| WO | 2008092958 A2 | 8/2008 |
| WO | 2008092959 A1 | 8/2008 |
| WO | 2008133702 A1 | 11/2008 |
| WO | 2008135098 A1 | 11/2008 |
| WO | 2008147600 A1 | 12/2008 |
| WO | 2008148714 A1 | 12/2008 |
| WO | 2008155145 A1 | 12/2008 |
| WO | 2008155377 A1 | 12/2008 |
| WO | 2009004026 A1 | 1/2009 |
| WO | 2009007287 A1 | 1/2009 |
| WO | 2009016635 A2 | 2/2009 |
| WO | 2009039013 A1 | 3/2009 |
| WO | 2009098291 A1 | 8/2009 |
| WO | 2009098306 A1 | 8/2009 |
| WO | 2009101130 A1 | 8/2009 |
| WO | 2009101145 A1 | 8/2009 |
| WO | 2009106517 A1 | 9/2009 |
| WO | 2009144272 A1 | 12/2009 |
| WO | 010003886 A1 | 1/2010 |
| WO | 2010003885 A1 | 1/2010 |
| WO | 2010030602 A1 | 3/2010 |
| WO | 2010034830 A1 | 4/2010 |
| WO | 2010051079 A2 | 5/2010 |
| WO | 2010072664 A1 | 7/2010 |
| WO | 2010080715 A1 | 7/2010 |
| WO | 2010084268 A1 | 7/2010 |
| WO | 2010112521 A1 | 10/2010 |
| WO | 2011012465 A1 | 2/2011 |
| WO | 2011015659 A1 | 2/2011 |
| WO | 2011121023 A1 | 10/2011 |
| WO | 2012041784 A1 | 4/2012 |
| WO | 2012041923 A2 | 4/2012 |
| WO | 2012045667 A2 | 4/2012 |
| WO | 2012107440 A1 | 8/2012 |
| WO | 2013057090 A1 | 4/2013 |
| WO | 2015094945 A1 | 6/2015 |

OTHER PUBLICATIONS

PCT/EP2012/070462 International Search Report and Written Opinion dated Nov. 22, 2012.
U.S. Appl. No. 13/652,722 Office Action dated Dec. 24, 2014.
U.S. Appl. No. 13/652,722 Office Action dated Jun. 3, 2016.
U.S. Appl. No. 13/652,722 Office Action dated May 7, 2015.
U.S. Appl. No. 13/652,722 Office Action dated Nov. 27, 2015.
"Why inset®?" inset® infusion set product overview. http://web.archive.org/web/20040906102448/http://www.infusion-set.com/Default.asp?ID=108; two pages, printed Jan. 9, 2008.

* cited by examiner

INFUSION TUBE SYSTEM AND METHOD FOR MANUFACTURE

RELATED APPLICATIONS

This application is a continuation application of, and claims the priority benefit of, U.S. application Ser. No. 15/282,825 entitled "INFUSION TUBE SYSTEM AND METHOD FOR MANUFACTURE," which was filed on Sep. 30, 2016, and which is a continuation of U.S. application Ser. No. 13/652,722 filed on Oct. 16, 2012, which claims the priority benefit of U.S. Provisional Application Ser. No. 61/548,871 filed on Oct. 19, 2011 and European Application No. 11185747.0 filed Oct. 19, 2011. Those applications are incorporated by reference herein in their entireties.

TECHNICAL FIELD

The present invention relates to an infusion tube system and a method for manufacture of an infusion tube system, in particular an infusion tube system for coupling to an infusion port of an infusion device.

BACKGROUND

Present tube systems, in particular tube systems for infusion, comprise a tube and a connector attached to an end of the tube in order to couple the tube to other devices, such as an infusion device or an inserter device.

Cost-effective manufacture of infusion tube systems for infusion devices requires low or reduced material costs and low or no scrap rate in the production process. Further, it may be desirable to reduce or remove one or more processes in the manufacture cycle.

SUMMARY

Thus there is a need for devices and methods for reducing material waste in production or manufacture of infusion tube systems. Further, there may be a need for infusion tube systems enabling use of simple infusion devices, e.g. infusion devices with simple coupling systems.

Accordingly, an infusion tube system is provided, the infusion tube system comprising an infusion tube and a connector attached to the infusion tube at an end of the infusion tube, the connector having a proximal end and comprising a connector body extending from a distal end to a proximal end along a center axis and defining a cavity, the connector body comprising an end wall with an inner surface, and at least one vent opening including a first vent opening, and a sidewall extending from the end wall along the center axis with an inner and outer surface. The connector comprises a membrane covering the at least one vent opening, the membrane being welded to the inner surface of the end wall along at least one welding seam including a first welding seam such that the membrane covers and seals the at least one vent opening.

It is an important advantage of the present invention that membrane material covering the vent openings has not been subject to substantial heat caused by the welding process, thereby ensuring that the membrane material function as intended leading to more effective manufacture of infusion tube systems due to reduced material waste. Further, the present invention enables a more effective manufacture of tube infusion system due to smaller number of defective tube infusions system and a reduced scrap rate.

Further disclosed is a method for manufacture of an infusion tube system comprising an infusion tube and a connector, the method comprising providing a connector with a connector body extending from a distal end to a proximal end along a center axis and defining a cavity, the connector body comprising an end wall with an inner surface, and at least one vent opening including a first vent opening, and a sidewall extending from the end wall along the center axis with an inner and outer surface. The method further comprises providing a membrane at the inner surface of the end wall, and welding the membrane to the inner surface of the end wall along at least one welding seam including a first welding seam such that the membrane covers and seals the at least one vent opening.

BRIEF DESCRIPTION OF THE DRAWINGS

The above and other features and advantages of the present invention will become readily apparent to those skilled in the art by the following detailed description of exemplary embodiments thereof with reference to the attached drawings, in which.

DETAILED DESCRIPTION OF ILLUSTRATIVE EMBODIMENTS

The figures are schematic and simplified for clarity, and they merely show details which are essential to the understanding of the invention, while other details have been left out. Throughout, the same reference numerals are used for identical or corresponding parts.

The infusion tube system comprises an infusion tube and a connector at an end, e.g. a first end, of the infusion tube. The connector may be adapted for coupling to an inlet or outlet port of an infusion device having a housing accommodating a pump device and a reservoir with medicine, e.g. insulin, or other infusion liquid.

The connector has a distal end, a proximal end and a connector body extending from a distal end to a proximal end of the connector body along a center axis and defining a cavity.

The connector body comprises an end wall with an inner surface, and at least one sidewall extending from the end wall along the center axis and having an inner and outer surface. The inner surface of the end wall and the sidewall define or at least partly define the cavity. The cavity may be cylindrical or at least partly cylindrical with a cross section of suitable size and shape, i.e. the inner surface of the sidewall may have a cross section perpendicular to the center axis, the cross section being substantially constant along at least a part of the center axis. In one or more embodiments, cross section areas of the cavity may increase towards the distal end of the connector. The cavity may be cylindrical with a circular or non-circular (oval, polygonal or elliptical) inner surface cross-section perpendicular to the center axis.

The end wall comprises at least one vent opening including a first vent opening. The at least one vent opening connects or communicates the cavity with the surroundings through the end wall and a membrane covering the at least one vent opening. The at least one vent opening may include a plurality of vent openings including the first vent opening and a second vent opening formed in the end wall. Further, a third and/or fourth vent opening may be formed in the end wall. A vent opening may have any suitable size and shape. In one or more embodiments, one or more vent openings are circular, elliptical, kidney-shaped or oval, e.g. with a diameter or maximum extension less than 8 mm, such as in the range from 0.5 mm to 5 mm. In one or more embodiments, one or more vent openings may have an area in the range from 0.3 $mm^2$ to 20 $mm^2$. The area of the respective vent openings depends e.g. on the number of vent openings in the end wall and the available inner surface area of the end wall. In one or more embodiments with three to six vent openings, the area of each vent opening may be in the range from 0.3 $mm^2$ to 2 $mm^2$. In one or more embodiments, with one or two vent openings, the area of the vent openings may be in the range from 1.0 $mm^2$ to 10 $mm^2$.

The connector comprises a membrane covering the at least one vent opening including the first vent opening and other vent openings if present. The membrane is welded to an inner surface defining the cavity. The membrane may be welded to the inner surface of the end wall such that the membrane covers and seals the at least one vent opening including the first vent opening and other vent openings if present. Thus air or other gasses must pass the membrane in order to flow from the cavity to the surroundings through the at least one vent opening, e.g. in order to equalize pressure between the cavity and the surroundings. The membrane enables pressure equalization of a cavity within an infusion device through the vent opening and at the same time providing a substantially liquid tight infusion device when the infusion tube system is connected to the infusion port of the infusion device.

The membrane is welded to the inner surface of the end wall along at least one welding seam including a first welding seam and optionally a second welding seam. The first welding seam and/or the second welding seam may form a closed curve. The first welding seam may surround at least the first vent opening. In one or more embodiments, the first welding seam surrounds all the vent openings in the end wall. In one or more embodiments, the second welding seam may if present form a closed curve surrounding a fluid path opening or a connector needle in the end wall.

The second welding seam may form a closed curve surrounding one or more vent openings including a second vent opening in the end wall.

The first welding seam may form a closed outer welding seam and the second welding seam may form a closed inner welding seam surrounded by the outer welding seam, wherein the membrane area between the inner welding seam and the outer welding seam covers at least one vent opening, e.g. the first vent opening. In one or more embodiments, the membrane area between an inner welding seam and an outer welding seam covers all vent openings in the end wall. Welding seams may cross each other.

In one or more embodiments welding seam(s), e.g. the first welding seam and/or a second welding seam, forms a closed curve surrounding one or more vent openings and wherein the connector needle or a fluid path opening in the end wall is arranged outside the closed curve of the welding seam.

A welding seam may have a suitable length which at least for an outer welding seam may depend on the number and configuration of vent openings to be surrounded. In one or more embodiments, the first welding seam may have a length in the range from 4 mm to about 100 mm, such as in the range from 10 mm to 50 mm, such as about 30 mm. The welding seam must be sufficiently wide to ensure sealing of the membrane to the inner surface of the cavity. On the other hand, the width of a welding seam is limited, e.g. in order to maximize the non-welded area of the membrane. Accordingly, a welding seam, e.g. the first welding seam and/or the second welding seam may have a width in the range from 0.1 mm to 3.0 mm, such as from 0.3 mm to 2.0 mm. In one or more embodiments, a welding seam width of 0.5 mm to 1 mm may be advantageous.

The total welding area being the sum of welding areas for respective welding seams may be less than 95% of the common area between the membrane and the inner surface of the end wall. In one or more embodiments, the total welding area is less than 90% of the common, i.e. overlapping, area between the membrane and the inner surface of the end wall.

The total welding area being the sum of welding areas for respective welding seams may be less than 90% of the area of the inner surface of the end wall. In one or more embodiments, the total welding area being the sum of welding areas for respective welding seams may be less than 70%, such as less than 50% of the area of the inner surface of the end wall.

The membrane is made of a suitable material in order to allow air or other gasses to flow through the membrane while substantially preventing liquid, e.g. water from the surroundings, to pass the membrane. The membrane may be air-permeable and may be made of or comprise a thermoplastic polymer, such as Polytetrafluoroethylene (PTFE). The membrane may be a hydrophobic membrane.

The membrane may be attached to the inner surface of the cavity by various welding methods, preferably by ultrasonic welding.

The connector may comprise a hollow connector needle with a distal end attached to the connector body and extending from the inner surface of the end wall into the cavity forming a fluid path between the infusion tube and the cavity. A fluid path opening may be formed in the inner surface of the end wall forming a fluid path between the infusion tube and the cavity.

The connector may comprise at least one annular protrusion including a first annular protrusion on the inner surface of the end wall, the first annular protrusion surrounding at least the first opening, wherein the membrane is welded to the inner surface of the end wall along the first annular protrusion.

The connector may comprise a support structure extending from the end wall in a proximal direction along the center axis. The support structure may define a support cavity accommodating at least a part of the infusion tube. Typically, a part of the outer surface of the infusion tube is attached to an inner surface of the support structure defining the support cavity.

FIG. 1-6 show different views of an infusion tube system according to the present invention. The infusion tube system 1 comprises an infusion tube 2 and a connector 4 attached to the infusion tube 2 at an end of the infusion tube 2. The connector 4 has a proximal end 6 and comprises a connector body 8 extending from a distal end 10 to a proximal end 12 along a center axis X and defining a cavity 14. The connector body 8 comprises an end wall 16 with an inner surface 18 and an outer surface 20. At least one vent opening including a first vent opening 22 is formed in the end wall 16. The connector 4 illustrated in FIGS. 1 and 2 has a second vent opening 24, and optionally a third vent opening 26 and/or a fourth vent opening 28 in the end wall 16. The connector body 8 comprises a sidewall 30 extending from the end wall 16 along the center axis X with an inner surface 32 and an outer surface 34. Further, the connector 4 comprises a membrane 36 covering the vent openings 22, 24, 26, 28. The membrane 36 is welded to the inner surface 18 of the end wall 16 along a first welding seam 38 and a second welding seam 40 such that the membrane 36 covers and seals the four vent openings 22, 24, 26, 28. The vent openings 22, 24, 26, 28 have a circular cross-section perpendicular to the center axis X with a diameter $D_1, D_2, D_3, D_4$, respectfully, of about 1 mm. The cavity 14 defined by the inner surfaces 18, 32 is cylindrical with a circular cross-section having a diameter of about 12 mm and a length of about 10 mm. The connector 4 optionally comprises a hollow connector needle 42 attached to the connector body 8 and extending from the inner surface 18 of the end wall 16 into the cavity 14. The connector needle 42 forms a fluid path from the flow channel in the infusion tube 2 to the distal end 44 of the hollow connector needle 42. In the absence of a connector needle, a fluid path opening in the end wall 16 may connect the flow channel of the infusion tube with the cavity 14.

Figure 1:
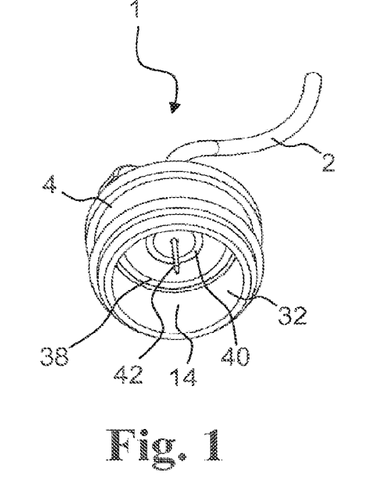
FIG. 1 is a first perspective view of an exemplary infusion tube system.
Figure 2:
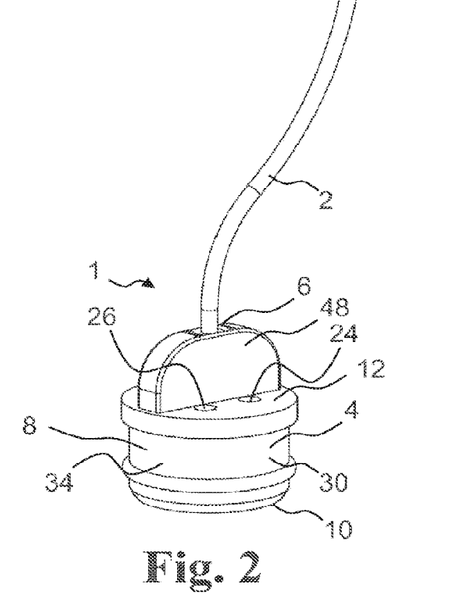
FIG. 2 is a second perspective view of the infusion tube system in FIG. 1.
Figure 3:
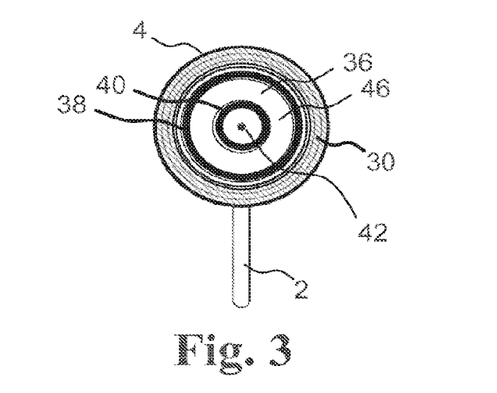
FIG. 3 is an end view of the infusion tube system in FIG. 1 seen from the distal end of the connector perpendicular to the center axis.
Figure 4:
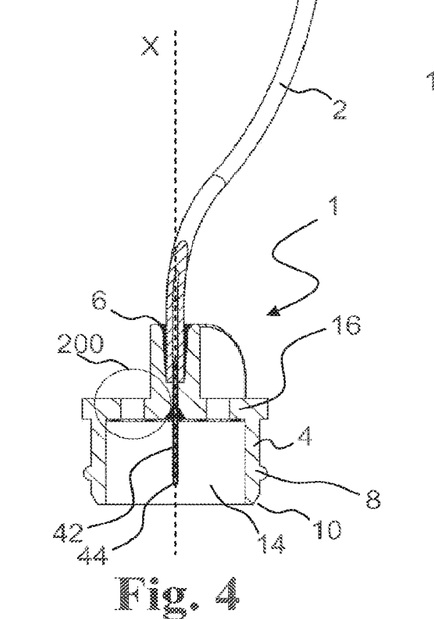
FIG. 4 is a cross section U-U of the infusion tube system in FIG. 1 as indicated in FIG. 5.
Figure 5:
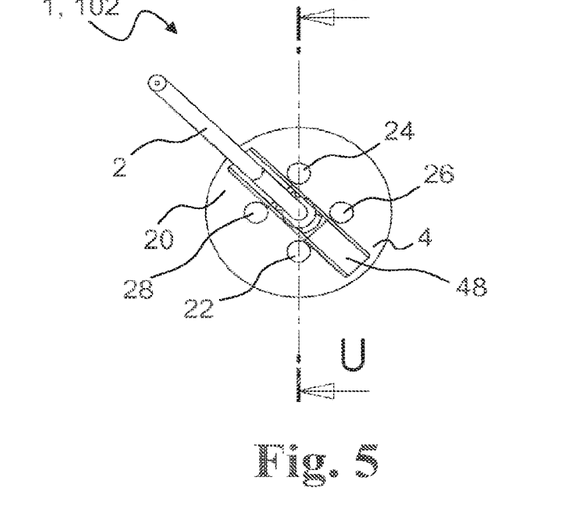
FIG. 5 shows an infusion tube system perpendicular to the center axis.
Figure 6:
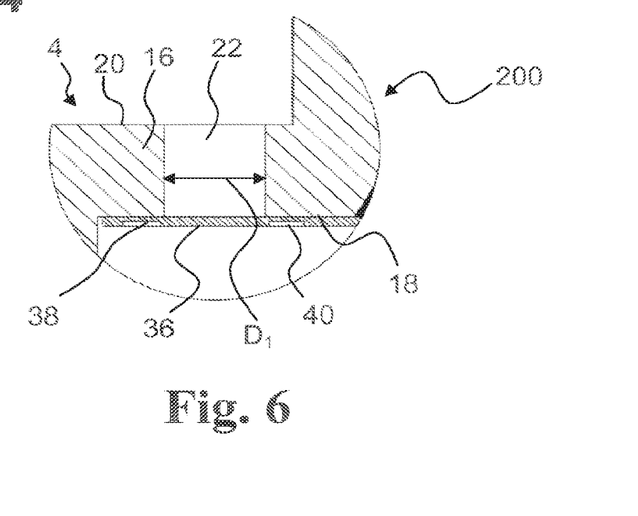
FIG. 6 is a detailed view of a part of the infusion tube system as indicated by the circle in FIG. 4.

The first welding seam 38 forms a closed curve in the form of a circle having a diameter in the range from 8 to 10 mm surrounding the first, second, third and fourth vent opening, and the second welding seam 40 forming a closed curve, e.g. a circle with a diameter e.g. of about 3.5 mm to 4.5 mm, surrounding the connector needle 42 and positioned on the inside of the vent openings as seen e.g. in the end view in FIG. 3 and in the detailed view in FIG. 6. The first welding seam 38 forms a closed outer welding seam and the second welding seam 40 forms a closed inner welding seam surrounded by the outer welding seam 38, wherein the membrane area 46 between the inner welding seam and the outer welding seam covers the vent openings in the end wall, i.e. the four vent openings 22, 24, 26, 28 in this configuration. The first and second welding seams each have a width about 1 mm.

The membrane 36 is circular with a diameter about the diameter of the inner surface of the end wall (e.g. ±15%). An opening may be formed in the membrane to allow the connector needle to pass therethrough.

The connector 4 comprises a support structure 48 extending from the end wall 16 in a proximal direction along the center axis. The support structure 48 defines a cavity accommodating at least a part of the infusion tube, the infusion tube being attached to the inner surface defining the cavity, e.g. by gluing. The outer surface of the support structure 48 is adapted for facilitating manual handling of the infusion tube system, e.g. when the connector is to be connected to a device, such as an infusion port of an infusion device.

Figure 7:
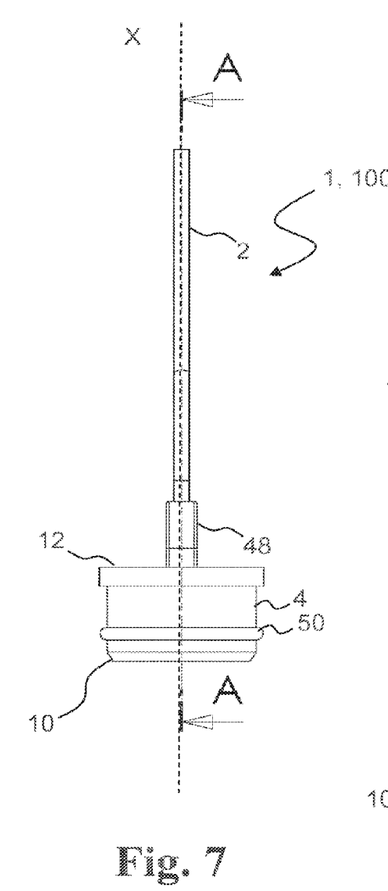
FIG. 7 is a side view of infusion tube systems.
Figure 8:
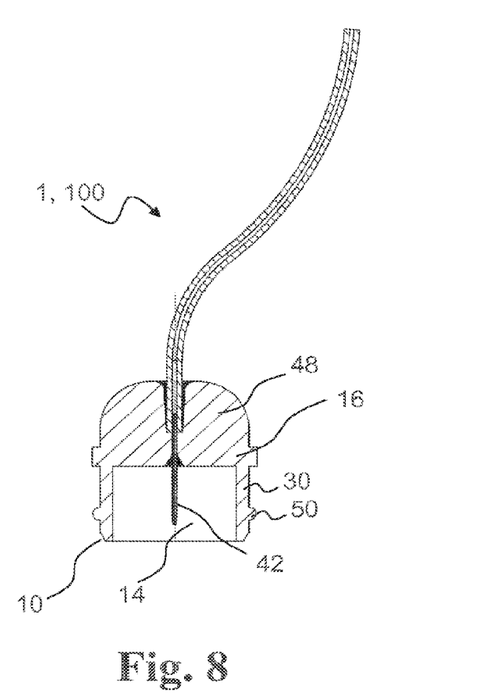
FIG. 8 is a cross section A-A of infusion tube systems as indicated in FIG. 7.
Figure 9:
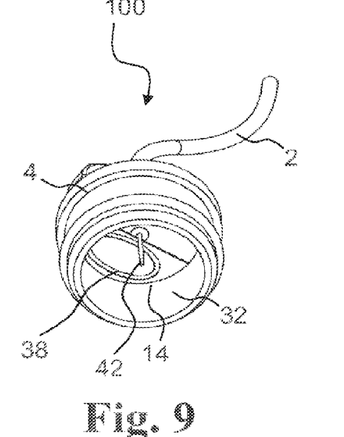
FIG. 9 is a first perspective view of an exemplary infusion tube system.
Figure 10:
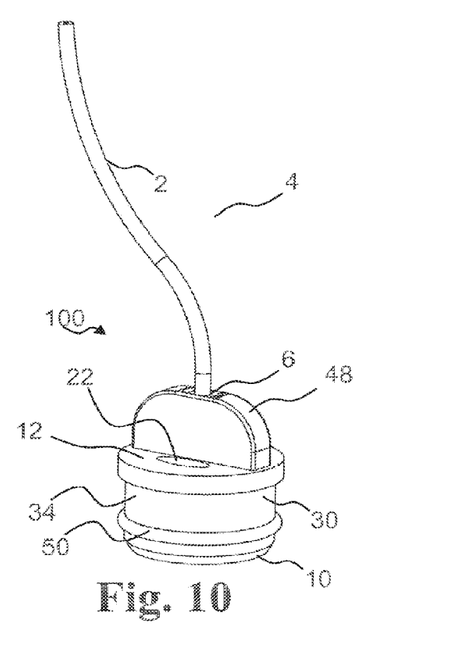
FIG. 10 is a second perspective view of the infusion tube system in FIG. 9.
Figure 11:
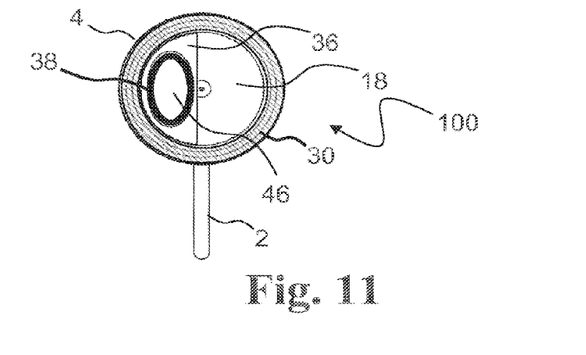
FIG. 11 is an end view of the infusion tube system in FIG. 9 seen from the distal end of the connector perpendicular to the center axis.
Figure 12:
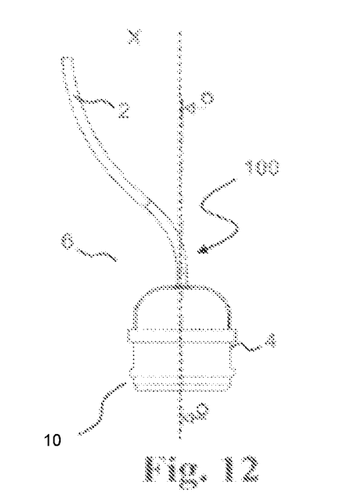
FIG. 12 is a side view of the infusion tube system of FIG. 9.
Figure 13:
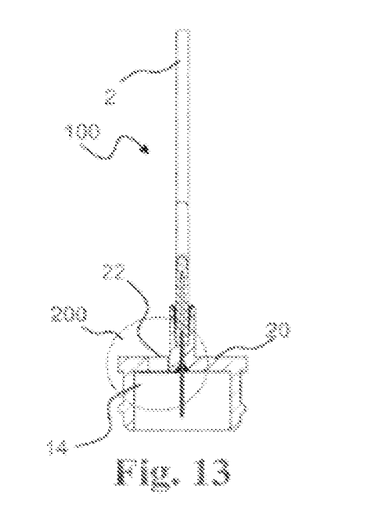
FIG. 13 is a cross section O-O of the infusion tube system of FIG. 9 as indicated in FIG. 12.
Figure 14:
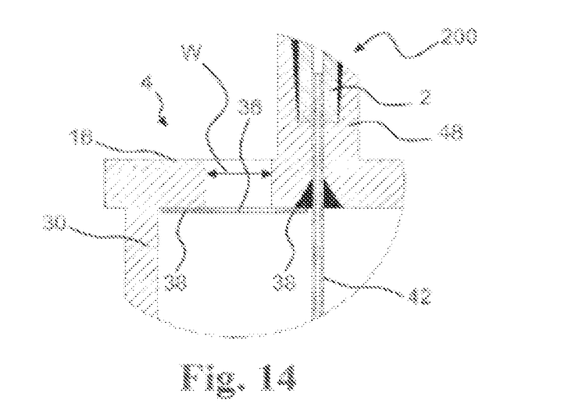
FIG. 14 is a detailed view of a part of the infusion tube system as indicated by the circle in FIG. 13.

FIGS. 7 and 8 is a sideview of infusion tube systems 1, 100 and a cross-section A-A as indicated. The infusion tube systems 1, 100 are shown without membrane 36. A sealing element 50 is formed as an annular protrusion on the outer surface 34 and perpendicular to the center axis X. The sealing element 50 may be formed as an integrated part of and in the same material as the connector body 8. In one or more embodiments, the sealing element may be molded to the connector body in a two-step molding process, e.g. in a resilient material to facilitate coupling and sealing of the connector 4 at an infusion port. In one or more embodiments, the sealing element may be an o-ring at least partly accommodated in an annular recess at the outer surface 34 of the sidewall 30.

FIGS. 9-14 show different views of an infusion tube system according to the present invention. The infusion tube system 100 only has a first vent opening 22 in the end wall 16. A first welding seam 38 forms a closed oval curve surrounding the first vent opening 22, thereby sealing the first vent opening with the membrane 36. The connector needle 42 is arranged outside the closed curve of the first welding seam 38.

The first vent opening 22 in the infusion tube system 100 is oval and having an area of about 1.5 $mm^2$ (W=1 mm and length L=2 mm) A single or limited number of vent openings may allow for a smaller membrane leading to material cost savings. The membrane 36 of infusion tube system 100 is about half the size of the membrane area in infusion tube system 1 as shown in FIG. 1-6.

Figure 15:
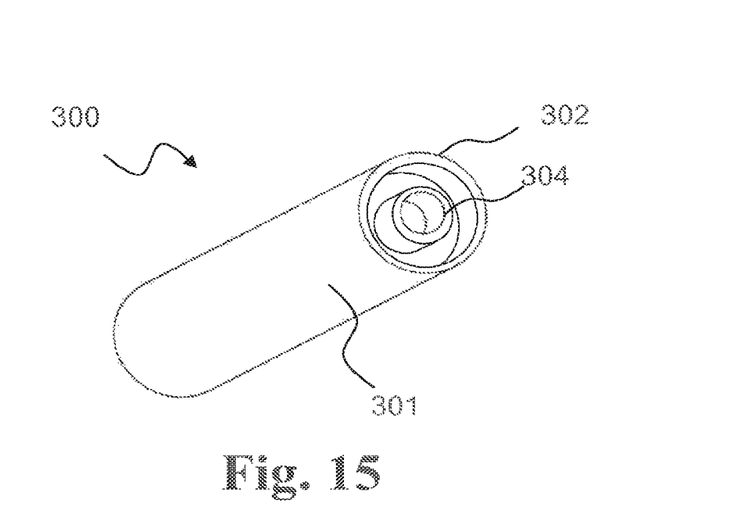
FIG. 15 is a perspective view of an exemplary weld horn used for manufacture of the infusion tube system of FIG. 1-6.

FIG. 15 shows a weld horn used for manufacture of the infusion tube system 1. The weld horn 300 comprises a body 301 with a first annular protrusion 302 and second annular protrusion 304 for forming the first welding seam 38 and the second welding seam 40, respectively of infusion tube system 1.

Figure 16:
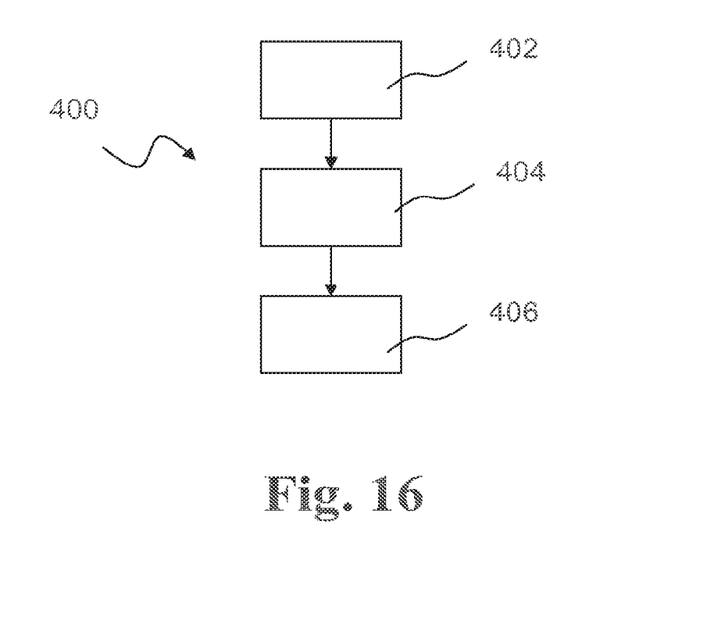
FIG. 16 schematically illustrates steps of the method according to the present invention.

FIG. 16 is a flow chart illustrating a method according to the invention namely a method for manufacture of an infusion tube system comprising an infusion tube and a connector. The method 400 comprises providing 402 a connector with a connector body extending from a distal end to a proximal end along a center axis and defining a cavity, the connector body comprising an end wall with an inner surface, and at least one vent opening including a first vent opening, and a sidewall extending from the end wall along the center axis with an inner and outer surface. Further, the method comprises providing 404 a membrane 36 at the inner surface of the end wall, and welding 406 by ultrasonic welding a membrane to the inner surface of the end wall along at least one welding seam including a first welding seam 38 such that the membrane covers and seals the at least one vent opening. Welding 406 comprises pressing the membrane between the connector body 8 and a weld horn 300 comprising at least one annular weld protrusion forming at least one welding seam.

Figure 17:
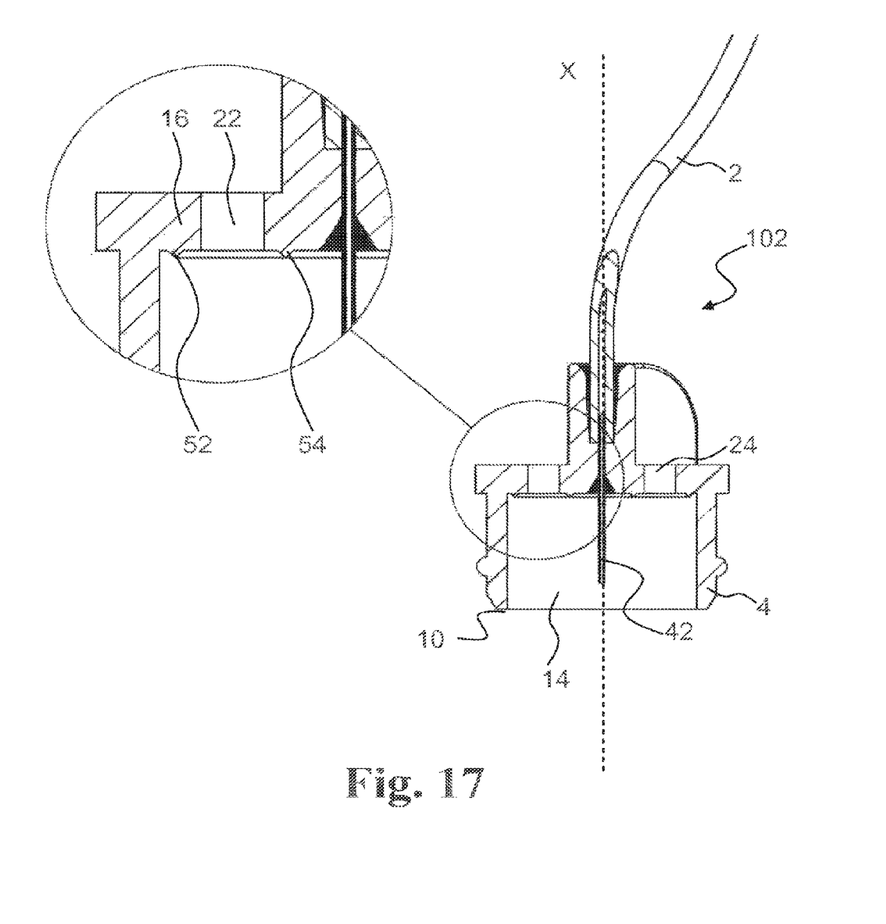
FIG. 17 is a cross section U-U of an exemplary infusion tube system as indicated in FIG. 5.

FIG. 17 shows a cross-section of an exemplary infusion tube system 102. For illustrative purposes, the membrane is not shown in FIG. 17. The connector 4 comprises at least one protrusion extending from the inner surface 18 of the end wall in the distal direction, i.e. towards the distal end 10. The at least one protrusion comprises a first protrusion 52 forming a circular or annular protrusion, e.g. surrounding the vent openings 22, 24, 26, 28. Further, a second protrusion 54 forms a circular or annular protrusion by the first protrusion, wherein the vent openings 22, 24, 26, 28 are positioned between the first protrusion 52 and the second protrusion 54 radially from the center axis. The protrusions 52, 54 may have a height, of at least 0.5 mm. In an embodiment similar to the infusion tube system 100, a first protrusion forming a dosed curve may surround one or more vent openings while the connector needle or a fluid path opening is positioned on the outside of the dosed curve formed by the first protrusion.

The support structure 48 and the connector body 8 may form an integrated unit, i.e. molded in a single process as illustrated in the figures.

It should be noted that in addition to the exemplary embodiments of the invention shown in the accompanying drawings, the invention may be embodied in different forms and should not be construed as limited to the embodiments set forth herein. Rather, these embodiments are provided so that this disclosure will be thorough and complete, and will fully convey the concept of the invention to those skilled in the art.

LIST OF REFERENCES 1, 100, 102 infusion tube system
2 infusion tube
4 connector
6 proximal end of connector
8 connector body
10 distal end of connector body
12 proximal end of connector body
14 cavity
16 end wall
18 inner surface of end wall
20 outer surface of end wall
22 first vent opening
24 second vent opening
26 third vent opening
28 fourth vent opening
30 sidewall
32 inner surface of side wall
34 outer surface of side wall
36 membrane
38 first welding seam
40 second welding seam
42 connector needle
44 distal end of connector needle
46 sealing membrane area
48 support structure
50 sealing element
52 first protrusion
54 second protrusion
200 detail view
300 weld horn
301 body
302 first annular protrusion
304 second annular protrusion
X center axis X

What is claimed is:

1. A connector for connecting an infusion tube to an infusion device, the connector comprising:
   a connector body extending around a center axis of the connector, wherein the connector body includes an end wall, a first vent opening that extends through the end wall, a membrane that covers the first vent opening at an inner surface of the end wall, and a first protrusion that extends away from the inner surface toward a distal end of the connector body, and wherein only the first protrusion defines a curve that completely surrounds the first vent opening;
   a cavity at least partially surrounded by the connector body; and
   a fluid path allowing fluid communication between the infusion tube and the cavity,
   wherein the fluid path is arranged outside of the curve and defined by a needle that lies on the center axis of the connector, and
   wherein the membrane extends outside of the curve to the needle.

2. The connector of claim 1, wherein the first vent opening is the only vent opening formed in the connector body.

3. The connector of claim 1, wherein the curve extends only partway around the center axis.

4. The connector of claim 1, wherein the inner surface has an annular portion that encircles the fluid path and defines a radially-outermost periphery of the inner surface relative to the center axis of the connector, and wherein the first protrusion is located radially inward of the annular portion relative to the center axis such that the first protrusion is located radially inward of, and does not define, the radially-outermost periphery of the inner surface.

5. The connector of claim 4, wherein the annular portion of the inner surface is flat along the radially-outermost periphery of the inner surface all the way around the center axis of the connector.

6. The connector of claim 5, wherein the first vent opening is the only vent opening formed in the connector body.

7. The connector of claim 1, further comprising a first welding seam located at the first protrusion that seals the first vent opening.

8. The connector of claim 7, wherein the first welding seam forms a closed curve surrounding at least the first vent opening.

9. The connector of claim 1, wherein the connector comprises a support structure extending from the end wall in a proximal direction, and wherein the support structure accommodates at least a part of the infusion tube.

10. The connector of claim 1, wherein the first protrusion has a height of at least 0.5 mm.

* * * * *